US012725708B2

(12) United States Patent
Nothacker et al.

(10) Patent No.: US 12,725,708 B2
(45) Date of Patent: Sep. 1, 2026

(54) METHOD AND SYSTEM FOR MONITORING INTOXICATION

(71) Applicant: KHN Solutions, LLC, San Francisco, CA (US)

(72) Inventors: Keith Harry Nothacker, San Francisco, CA (US); Pauline Anne Basaran, Corte Madera, CA (US); Stacey Ilene Rettus, Greenbrae, CA (US); Michael Jurgen Strasser, San Francisco, CA (US); Imraan Aziz, San Francisco, CA (US); John Paul Walton, San Francisco, CA (US); Zachary Michael Saul, San Francisco, CA (US)

(73) Assignee: KHN Solutions, LLC, San Francisco, CA (US)

( * ) Notice: Subject to any disclaimer, the term of this patent is extended or adjusted under 35 U.S.C. 154(b) by 0 days.

(21) Appl. No.: 18/906,782

(22) Filed: Oct. 4, 2024

(65) Prior Publication Data

US 2025/0029726 A1 Jan. 23, 2025

Related U.S. Application Data

(63) Continuation of application No. 18/126,839, filed on Mar. 27, 2023, now abandoned, which is a (Continued)

(51) Int. Cl.
*G16H 50/20* (2018.01)
*A61B 5/00* (2006.01)

(Continued)

(52) U.S. Cl.
CPC ........... *G16H 50/20* (2018.01); *A61B 5/0022* (2013.01); *A61B 5/0077* (2013.01); *A61B 5/082* (2013.01);

(Continued)

(58) Field of Classification Search
CPC ...... G16H 50/20; G16H 50/70; A61B 5/0022; A61B 5/0077; A61B 5/082; A61B 5/097;

(Continued)

(56) References Cited

U.S. PATENT DOCUMENTS

| | | | |
|---|---|---|---|
| 3,824,538 | A | 7/1974 | Slemp |
| 4,487,055 | A | 12/1984 | Wolf |

(Continued)

FOREIGN PATENT DOCUMENTS

| | | | |
|---|---|---|---|
| FR | 2975522 | A1 | 11/2012 |
| KR | 100673261 | B1 | 1/2007 |

(Continued)

OTHER PUBLICATIONS

"STIC Search Results. 15205876-528781-Search Results.pdf, Sep. 18, 2003.", Oct. 11, 2017 00:00:00.0.

(Continued)

*Primary Examiner* — Ryan W Sherwin
(74) *Attorney, Agent, or Firm* — Jeffrey Schox

(57) ABSTRACT

A method and system for monitoring a user's intoxication including receiving a set of signals, derived from a set of samples collected from the user at a set of time points; providing a sobriety task to the user proximal to a time point of the set of time points; generating a performance dataset characterizing performance of the sobriety task by the user; receiving a supplementary dataset characterizing a demographic profile of the user and/or a physiological state of the user; determining a set of values of an intoxication metric, derived from the set of signals; generating a predicted temporal profile of the intoxication metric for the user based upon the set of values, the set of time points, and the supplementary dataset; generating an analysis of the user's (Continued)

sobriety based upon the performance dataset and the predicted temporal profile; and providing a notification to the user based upon the analysis.

20 Claims, 10 Drawing Sheets

Related U.S. Application Data continuation of application No. 17/839,728, filed on Jun. 14, 2022, now Pat. No. 11,646,120, which is a continuation of application No. 15/979,220, filed on May 14, 2018, now Pat. No. 11,393,588, which is a continuation of application No. 15/294,998, filed on Oct. 17, 2016, now Pat. No. 9,996,673, which is a continuation of application No. 15/212,600, filed on Jul. 18, 2016, now Pat. No. 9,740,827, which is a continuation of application No. 14/728,573, filed on Jun. 2, 2015, now Pat. No. 9,600,632, which is a continuation of application No. 14/470,376, filed on Aug. 27, 2014, now Pat. No. 9,076,317, which is a continuation of application No. 14/169,029, filed on Jan. 30, 2014, now Pat. No. 8,878,669.

(60) Provisional application No. 61/812,704, filed on Apr. 16, 2013, provisional application No. 61/759,390, filed on Jan. 31, 2013.

(51) Int. Cl.

| | |
|---|---|
| ***A61B 5/08*** | (2006.01) |
| ***A61B 5/097*** | (2006.01) |
| ***A61B 5/18*** | (2006.01) |
| ***G01N 33/497*** | (2006.01) |
| ***G01N 33/98*** | (2006.01) |
| ***G08B 21/02*** | (2006.01) |
| ***G16H 50/70*** | (2018.01) |
| ***G16Z 99/00*** | (2019.01) |
| *A61B 10/00* | (2006.01) |

(52) U.S. Cl.

CPC ................ *A61B 5/097* (2013.01); *A61B 5/18* (2013.01); *A61B 5/4023* (2013.01); *A61B 5/4845* (2013.01); *A61B 5/486* (2013.01); *A61B 5/4863* (2013.01); *A61B 5/7275* (2013.01); *A61B 5/743* (2013.01); *A61B 5/7445* (2013.01); *G01N 33/4972* (2013.01); *G01N 33/98* (2013.01); *G08B 21/02* (2013.01); *G16H 50/70* (2018.01); *G16Z 99/00* (2019.02); *A61B 2010/0009* (2013.01); *A61B 2010/0087* (2013.01); *A61B 2562/0219* (2013.01)

(58) Field of Classification Search

CPC ....... A61B 5/18; A61B 5/4023; A61B 5/4845; A61B 5/486; A61B 5/4863; A61B 5/7275; A61B 5/743; A61B 5/7445; A61B 2010/0009; A61B 2010/0087; A61B 2562/0219; G01N 33/4972; G01N 33/98; G08B 21/02; G16Z 99/00

See application file for complete search history.

(56) References Cited

U.S. PATENT DOCUMENTS

| | | | | |
|---|---|---|---|---|
| 4,738,333 | A | 4/1988 | Collier et al. | |
| 4,749,553 | A | 6/1988 | Lopez et al. | |
| 4,902,628 | A | 2/1990 | Blair | |
| 4,914,038 | A | 4/1990 | Jewitt | |
| 4,996,161 | A | 2/1991 | Conners et al. | |
| 5,157,601 | A | 10/1992 | Jones et al. | |
| D333,441 | S | 2/1993 | Greene | |
| 5,216,415 | A | 6/1993 | Ono et al. | |
| 5,220,919 | A | 6/1993 | Phillips et al. | |
| 5,248,617 | A | 9/1993 | De | |
| 5,274,550 | A * | 12/1993 | Greenlee | G16H 40/63 73/23.3 |
| 5,291,898 | A | 3/1994 | Wolf | |
| 5,416,468 | A | 5/1995 | Baumann | |
| 5,426,415 | A | 6/1995 | Prachar et al. | |
| 5,433,863 | A | 7/1995 | Braden et al. | |
| D362,642 | S | 9/1995 | Howse | |
| D381,885 | S | 8/1997 | Lane | |
| 5,787,885 | A | 8/1998 | Lemelson | |
| 5,834,626 | A | 11/1998 | De et al. | |
| 5,944,661 | A | 8/1999 | Swette et al. | |
| 6,017,308 | A | 1/2000 | Fults | |
| 6,026,674 | A | 2/2000 | Gammenthaler | |
| 6,075,444 | A | 6/2000 | Sohege et al. | |
| 6,097,286 | A | 8/2000 | Discenzo | |
| 6,229,908 | B1 | 5/2001 | Edmonds et al. | |
| 6,433,863 | B1 | 8/2002 | Weiss | |
| 6,454,723 | B1 | 9/2002 | Montagnino | |
| 6,556,905 | B1 | 4/2003 | Mittelsteadt et al. | |
| 6,608,399 | B2 | 8/2003 | Mcconnell et al. | |
| 6,726,636 | B2 | 4/2004 | Der et al. | |
| 6,748,792 | B1 | 6/2004 | Freund et al. | |
| 6,824,520 | B2 | 11/2004 | Orr et al. | |
| 6,853,956 | B2 | 2/2005 | Ballard et al. | |
| 6,858,182 | B1 | 2/2005 | Ito et al. | |
| RE38,728 | E | 4/2005 | Katzman et al. | |
| 6,899,683 | B2 | 5/2005 | Mault et al. | |
| 6,956,484 | B2 | 10/2005 | Crespo | |
| 6,958,691 | B1 | 10/2005 | Anderson et al. | |
| 6,968,375 | B1 | 11/2005 | Brown | |
| D521,885 | S | 5/2006 | Eddy et al. | |
| D530,424 | S | 10/2006 | Manser et al. | |
| D539,683 | S | 4/2007 | Shaw et al. | |
| D539,684 | S | 4/2007 | Kitamura et al. | |
| 7,204,335 | B2 | 4/2007 | Stewart et al. | |
| 7,256,700 | B1 | 8/2007 | Ruocco et al. | |
| 7,311,665 | B2 | 12/2007 | Hawthorne et al. | |
| 7,341,693 | B2 | 3/2008 | Der et al. | |
| 7,451,852 | B2 | 11/2008 | Stewart et al. | |
| 7,462,149 | B2 | 12/2008 | Hawthorne et al. | |
| D586,677 | S | 2/2009 | Nothacker et al. | |
| D603,281 | S | 11/2009 | Gonzalez | |
| 7,611,461 | B2 | 11/2009 | Hawthorne et al. | |
| 7,611,611 | B2 | 11/2009 | Belt | |
| D606,434 | S | 12/2009 | Castrodale et al. | |
| 7,636,047 | B1 | 12/2009 | Sempek | |
| 7,641,611 | B2 | 1/2010 | Hawthorne et al. | |
| 7,823,681 | B2 | 11/2010 | Crespo et al. | |
| 7,930,927 | B2 | 4/2011 | Cooper et al. | |
| 7,934,577 | B2 | 5/2011 | Walter et al. | |
| 8,040,233 | B2 | 10/2011 | Adappa et al. | |
| 8,078,334 | B2 | 12/2011 | Goodrich | |
| 8,126,735 | B2 | 2/2012 | Dicks et al. | |
| 8,165,824 | B2 | 4/2012 | Iiams et al. | |
| 8,224,608 | B1 | 7/2012 | Son et al. | |
| 8,240,419 | B2 | 8/2012 | Zimmermann et al. | |
| 8,258,968 | B2 | 9/2012 | Ghazarian et al. | |
| 8,280,436 | B2 | 10/2012 | Harris | |
| 8,317,697 | B2 | 11/2012 | Hawthorne et al. | |
| 8,336,665 | B1 | 12/2012 | Saunders | |
| 8,359,901 | B2 | 1/2013 | Freund et al. | |
| 8,370,027 | B2 | 2/2013 | Pettersson et al. | |
| 8,381,573 | B2 | 2/2013 | Keays | |
| 8,453,492 | B2 | 6/2013 | Tsuzuki et al. | |
| 8,466,796 | B1 | 6/2013 | Mejia et al. | |
| 8,505,360 | B2 | 8/2013 | Ruocco et al. | |
| 8,525,668 | B1 | 9/2013 | Alouani et al. | |
| 8,549,318 | B2 | 10/2013 | White et al. | |
| 8,560,010 | B2 | 10/2013 | Koehn | |
| 8,590,364 | B2 | 11/2013 | Lopez et al. | |
| 8,657,744 | B2 | 2/2014 | Rompa et al. | |
| 8,693,597 | B2 | 4/2014 | Sexton et al. | |

(56) References Cited

U.S. PATENT DOCUMENTS 8,701,814 B2 4/2014 Saunders
8,707,758 B2 4/2014 Keays
D705,100 S 5/2014 Nothacker et al.
8,795,187 B2 8/2014 Morley et al.
8,808,228 B2 8/2014 Brister et al.
8,814,804 B2 8/2014 Walden et al.
8,844,337 B2 9/2014 Kountotsis et al.
8,849,387 B2 9/2014 Gilbert et al.
8,862,152 B1 10/2014 Buchholz et al.
8,878,669 B2 11/2014 Nothacker et al.
8,899,748 B1 12/2014 Migdal
8,920,725 B2 12/2014 Withrow et al.
8,941,501 B1 1/2015 Debijl
8,957,771 B2 2/2015 Arringdale et al.
D724,980 S 3/2015 Nothacker et al.
D727,763 S 4/2015 Nothacker et al.
D727,764 S 4/2015 Nothacker et al.
9,011,657 B2 4/2015 Parselle et al.
9,020,773 B2 4/2015 Son et al.
9,035,777 B2 5/2015 Bangera et al.
9,042,615 B1 5/2015 Bradley et al.
D731,341 S 6/2015 Kobayakawa
9,045,101 B2 6/2015 Phelan
9,063,120 B2 6/2015 Park
9,076,317 B2 7/2015 Nothacker et al.
9,095,251 B2 8/2015 Purks et al.
9,138,167 B1 9/2015 Leydon
9,192,324 B2 11/2015 Phillips et al.
9,192,334 B2 11/2015 Nothacker et al.
9,228,997 B2 1/2016 Keays
9,239,323 B2 1/2016 Keays
9,241,054 B1 1/2016 Roberts
9,241,659 B2 1/2016 Rompa et al.
9,241,661 B2 1/2016 Shnaper et al.
9,250,228 B2 2/2016 Nothacker et al.
9,278,696 B2 3/2016 Yi et al.
9,301,719 B2 4/2016 Abreu
9,316,614 B2 4/2016 Stock et al.
9,398,858 B2 7/2016 Phillips et al.
9,417,232 B2 8/2016 Keays et al.
9,442,103 B1 9/2016 Goad
9,481,245 B2 11/2016 Nelson
9,489,487 B2 11/2016 Hawthorne et al.
9,609,921 B1 4/2017 Feinstein
9,643,186 B1 5/2017 Ahmad et al.
9,662,065 B2 5/2017 Nothacker et al.
9,707,845 B1 7/2017 Nienhouse
9,746,456 B2 8/2017 Keays
9,781,984 B2 10/2017 Baranski et al.
9,788,772 B2 10/2017 Nothacker et al.
9,820,114 B2 11/2017 Greenhut et al.
9,829,480 B2 11/2017 Wojcik et al.
9,848,815 B2 12/2017 Abreu
9,855,000 B2 1/2018 Lansdorp et al.
9,867,539 B2 1/2018 Heikenfeld et al.
9,872,649 B2 1/2018 Nothacker et al.
9,881,997 B2 1/2018 Sakata et al.
9,915,644 B2 3/2018 Nothacker et al.
9,922,508 B2 3/2018 Keays et al.
10,040,349 B2 8/2018 Devries et al.
10,154,460 B1 12/2018 Miller et al.
10,182,752 B2 1/2019 Nothacker et al.
10,352,923 B2 7/2019 Nothacker et al.
10,631,767 B2 4/2020 Nothacker et al.
10,987,038 B2 4/2021 Nothacker et al.
11,006,895 B2 5/2021 Nothacker et al.
11,278,222 B2 3/2022 Moeller et al.
11,324,449 B2 5/2022 Nothacker et al.
11,471,079 B2 10/2022 Nothacker et al.
11,602,306 B2 3/2023 Nothacker
11,646,120 B2 5/2023 Nothacker et al.
11,674,949 B2 6/2023 Moeller
2002/0008966 A1 1/2002 Fjelstad et al.
2002/0084130 A1 7/2002 Der et al.
2002/0089660 A1 7/2002 Weiss
2002/0128769 A1 9/2002 Der et al.
2002/0140289 A1 10/2002 Mcconnell et al.
2002/0143267 A1 10/2002 Montagnino
2003/0028120 A1 2/2003 Mault et al.
2003/0036823 A1 2/2003 Mahvi
2003/0116159 A1 6/2003 Orr et al.
2003/0117287 A1 6/2003 Crespo
2003/0146841 A1 8/2003 Koenig
2003/0176803 A1 9/2003 Gollar
2003/0177119 A1 9/2003 Cole
2003/0183437 A1 10/2003 Mendoza
2003/0208110 A1 11/2003 Mault et al.
2004/0081582 A1 4/2004 Brooke
2004/0233058 A1 11/2004 Dodds
2004/0233061 A1 11/2004 Johns
2004/0236199 A1 11/2004 Hawthorne et al.
2004/0239510 A1* 12/2004 Karsten .................. B60R 25/25 340/576
2004/0242976 A1 12/2004 Abreu
2005/0053523 A1 3/2005 Brooke
2005/0124694 A1 6/2005 Vanmoor
2005/0124906 A1* 6/2005 Childre ............... A61B 5/0816 600/529
2005/0184870 A1 8/2005 Galperin et al.
2005/0230175 A1 10/2005 Brown et al.
2005/0241871 A1 11/2005 Stewart et al.
2006/0058697 A1 3/2006 Mochizuki et al.
2006/0182661 A1 8/2006 Aquila
2006/0193749 A1 8/2006 Ghazarian et al.
2006/0217624 A1 9/2006 Myklebust et al.
2006/0217625 A1 9/2006 Forrester
2006/0237252 A1 10/2006 Mobley et al.
2006/0237253 A1 10/2006 Mobley et al.
2006/0282344 A1 12/2006 Brown
2006/0293613 A1 12/2006 Fatehi et al.
2007/0024454 A1 2/2007 Singhal
2007/0050127 A1 3/2007 Kellum et al.
2007/0077176 A1 4/2007 Lambert et al.
2007/0093725 A1 4/2007 Shaw
2007/0107728 A1 5/2007 Ricciardelli et al.
2007/0144812 A1 6/2007 Stewart et al.
2007/0296601 A1 12/2007 Sultan et al.
2008/0045806 A1 2/2008 Keppler
2008/0097793 A1 4/2008 Dicks et al.
2008/0169924 A1 7/2008 Belden
2008/0183388 A1 7/2008 Goodrich
2008/0216561 A1 9/2008 Cooper et al.
2008/0262469 A1 10/2008 Brister et al.
2008/0294059 A1* 11/2008 Arias .................... A61B 5/082 600/532
2009/0043409 A1 2/2009 Ota
2009/0054799 A1 2/2009 Vrtis et al.
2009/0060287 A1 3/2009 Hyde et al.
2009/0090577 A1 4/2009 Takahashi et al.
2009/0111486 A1 4/2009 Burstrom
2009/0164141 A1 6/2009 Lee
2009/0182216 A1 7/2009 Roushey et al.
2009/0187111 A1 7/2009 Reilly et al.
2009/0201138 A1 8/2009 Ghazarian et al.
2009/0212957 A1 8/2009 Burris
2009/0293589 A1 12/2009 Freund et al.
2009/0309711 A1 12/2009 Adappa et al.
2009/0325639 A1 12/2009 Koehn
2010/0010689 A1 1/2010 Yasushi et al.
2010/0012417 A1 1/2010 Walter et al.
2010/0036592 A1 2/2010 Osaki et al.
2010/0108425 A1 5/2010 Crespo et al.
2010/0121502 A1 5/2010 Katayama et al.
2010/0152976 A1 6/2010 White et al.
2010/0234064 A1 9/2010 Harris
2010/0268425 A1 10/2010 Pettersson et al.
2010/0274411 A1 10/2010 Ozaki
2010/0294583 A1 11/2010 Biondo et al.
2010/0310011 A1 12/2010 Sexton et al.
2010/0328066 A1 12/2010 Walker et al.
2011/0079073 A1 4/2011 Keays
2011/0266160 A1 11/2011 Campbell et al.
2011/0291827 A1 12/2011 Baldocchi et al.
2011/0304465 A1 12/2011 Boult et al.

(56) References Cited

U.S. PATENT DOCUMENTS

2011/0308297 A1 12/2011 Tsuzuki et al.
2011/0309932 A1 12/2011 Arringdale et al.
2012/0020837 A1 1/2012 Withrow et al.
2012/0031165 A1 2/2012 Ruocco et al.
2012/0031166 A1 2/2012 Lopez et al.
2012/0075094 A1 3/2012 Keays
2012/0130261 A1 5/2012 Fujita et al.
2012/0132524 A1 5/2012 Parselle et al.
2012/0157871 A1 6/2012 Walden et al.
2012/0291517 A1* 11/2012 Son .................... G01N 33/4972 73/23.3
2012/0330175 A1 12/2012 Phillips et al.
2013/0006068 A1 1/2013 Gemer et al.
2013/0021153 A1 1/2013 Keays
2013/0035602 A1 2/2013 Gemer
2013/0111979 A1 5/2013 Park
2013/0123570 A1 5/2013 Ly et al.
2013/0144190 A1 6/2013 Bruce et al.
2013/0150727 A1 6/2013 Phillips et al.
2013/0192338 A1 8/2013 Mayer et al.
2013/0218039 A1 8/2013 Sotos et al.
2013/0231871 A1 9/2013 Hok et al.
2013/0253360 A1 9/2013 Wang et al.
2013/0277134 A1 10/2013 Morley et al.
2013/0281873 A1 10/2013 Evans et al.
2013/0282321 A1 10/2013 Son et al.
2013/0305808 A1 11/2013 Yoo
2014/0003676 A1 1/2014 Baughman et al.
2014/0012143 A1 1/2014 Gilbert et al.
2014/0032596 A1 1/2014 Fish et al.
2014/0052567 A1 2/2014 Bhardwaj et al.
2014/0055268 A1 2/2014 Bangera et al.
2014/0055588 A1 2/2014 Bangera et al.
2014/0055589 A1 2/2014 Bangera et al.
2014/0059066 A1 2/2014 Koloskov
2014/0062703 A1 3/2014 Purks et al.
2014/0062722 A1 3/2014 Ofir et al.
2014/0076022 A1 3/2014 Ohlsson et al.
2014/0086590 A1 3/2014 Ganick et al.
2014/0135612 A1 5/2014 Yuen et al.
2014/0139665 A1 5/2014 Venkata et al.
2014/0155777 A1 6/2014 Kong
2014/0165697 A1* 6/2014 Mochizuki ......... G01N 33/4972 73/23.3
2014/0165698 A1 6/2014 Mochizuki et al.
2014/0188398 A1 7/2014 Cohen et al.
2014/0204334 A1 7/2014 Stoll
2014/0210627 A1 7/2014 Nothacker et al.
2014/0234172 A1 8/2014 Burgi et al.
2014/0240132 A1 8/2014 Bychkov
2014/0273858 A1 9/2014 Panther et al.
2014/0281523 A1 9/2014 Golino
2014/0303836 A1 10/2014 Phelan
2014/0311215 A1 10/2014 Keays et al.
2014/0335905 A1 11/2014 Bhoot
2014/0358020 A1 12/2014 Park et al.
2014/0361900 A1 12/2014 Nothacker et al.
2014/0365142 A1 12/2014 Baldwin
2014/0371603 A1 12/2014 Fujita et al.
2015/0025407 A1 1/2015 Eichler et al.
2015/0084774 A1 3/2015 Wojcik et al.
2015/0164416 A1 6/2015 Nothacker et al.
2015/0197151 A1 7/2015 Ballard, Jr.
2015/0216448 A1 8/2015 Lotan et al.
2015/0251660 A1 9/2015 Nelson
2015/0325104 A1 11/2015 Greenhut et al.
2015/0359469 A1 12/2015 Jacobs et al.
2015/0360696 A1 12/2015 Yi et al.
2016/0021228 A1 1/2016 Roberts
2016/0284200 A1 9/2016 Song et al.
2016/0318521 A1 11/2016 Nothacker et al.
2016/0324442 A1 11/2016 Zdeblick
2016/0338627 A1 11/2016 Lansdorp et al.
2016/0349239 A1 12/2016 Chien
2017/0000382 A1 1/2017 Leydon
2017/0079574 A1 3/2017 Rodriguez Restrepo et al.
2017/0086714 A1 3/2017 Nothacker et al.
2017/0086743 A1 3/2017 Bushnell et al.
2017/0103166 A1 4/2017 Oh et al.
2017/0231571 A1 8/2017 Rogers et al.
2017/0292926 A1 10/2017 Mayer et al.
2017/0303819 A1 10/2017 Nothacker et al.
2017/0313189 A1 11/2017 Walter et al.
2017/0354354 A1 12/2017 Nothacker et al.
2018/0049668 A1 2/2018 Defant et al.
2018/0064402 A1 3/2018 Leydon
2018/0074029 A1 3/2018 Devries et al.
2018/0074030 A1 3/2018 Devries et al.
2018/0085058 A1 3/2018 Chakravarthi et al.
2018/0086264 A1 3/2018 Pedersen
2018/0101721 A1 4/2018 Nienhouse
2018/0164285 A1 6/2018 Nothacker et al.
2018/0184920 A1 7/2018 Rabinovich et al.
2018/0209955 A1 7/2018 Moeller
2018/0263538 A1 9/2018 Heikenfeld et al.
2018/0347493 A1 12/2018 Tascillo et al.
2019/0246958 A1 8/2019 Moeller et al.
2019/0290197 A1 9/2019 Nothacker et al.
2020/0101982 A1 4/2020 Bowers et al.
2020/0124589 A1 4/2020 Gonzales
2021/0100493 A1 4/2021 Ben Oren et al.
2021/0128060 A1 5/2021 Sarcinelli et al.
2022/0039478 A1 2/2022 Lavanchy et al.
2022/0125227 A9 4/2022 Brewster et al.
2022/0192597 A1 6/2022 Feldman
2022/0240849 A1 8/2022 Spector et al.
2023/0138641 A1 5/2023 Graham et al.
2023/0190188 A1 6/2023 Nothacker et al.
2024/0008812 A1 1/2024 Benson et al.
2024/0306937 A1 9/2024 Keays et al.
2024/0310358 A1 9/2024 Keays et al.
2024/0324893 A1 10/2024 Banos et al.

FOREIGN PATENT DOCUMENTS

KR 20110038453 A 4/2011
WO 2017165709 A1 9/2017

OTHER PUBLICATIONS

Kim, J. , et al., "Noninvasive alcohol monitoring using a wearable tattoo-based iontophoretic-biosensing system", ACS Sensors. Jul. 12, 2016. vol. 1. No. 8; abstract.

Kuswandi, B. , et al., "A simple visual ethanol biosensor based on alcohol oxidase immobilized onto polyaniline film for halal verification of fermented beverage samples", Sensors. 2014. vol. 14. No. 2; p. 2144, figure 6.

Nothacker, Keith Harry, et al., "Method and System for Detecting and Maintaining Performance of an Alcohol Sensing Device", U.S. Appl. No. 18/922,156, filed Oct. 21, 2024.

Zettl, Robert J., "The Determination of Blood Alcohol Concentration by Transdermal Measurement", Commissioned by Alcohol Monitoring Systems, Inc., Highlands Ranch, Colorado, Jul. 2002, 13 pages.

* cited by examiner

S155

202

Date/Time 8/21/2012 9:15PM

You blew: 0.03

State: Extroversion/Euphoria

Did you wait
20 Minutes?

Store My
Data

205

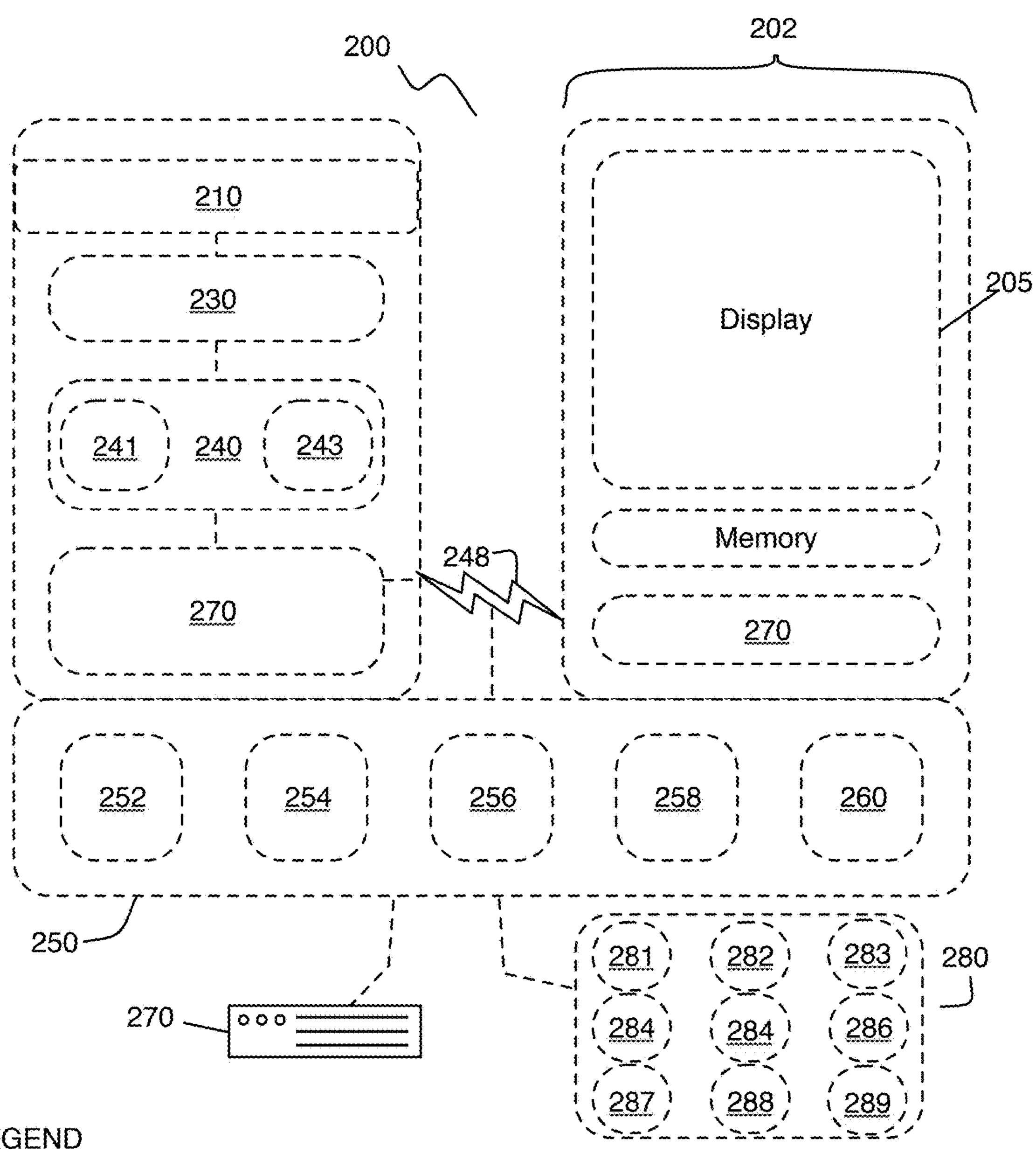

LEGEND

200 System 201 Breathalyzer Unit 202 Mobile Device 205 User interface
210 Sample Receiving Module 230 Sample Processing Module
240 Electronics Subsystem 241 Power Module 243 Conditioning Module
248 Data Link 250 Processor 252 First Module 254 Second Module
256 Third Module 258 Fourth Module 260 Fifth Module
270 Storage Module 280 Supplementary Sensing Module 281 Image Sensor
282 Accelerometer 283 Gyroscope 284 Location Sensor
285 Biometric Sensor 286 Manual Input Module 287 Aggregation Module
288 Object Recognition Module 289 Text Recognition Module

FIGURE 7A

METHOD AND SYSTEM FOR MONITORING INTOXICATION

CROSS-REFERENCE TO RELATED APPLICATIONS

This application is a continuation of U.S. application Ser. No. 18/126,839, filed 27 Mar. 2023, which is a continuations of U.S. application Ser. No. 17/839,728, filed 14 Jun. 2022 which is a continuation of U.S. application Ser. No. 15/979,220, filed 14 May 2018, which is a continuation of U.S. application Ser. No. 15/294,998, filed 17 Oct. 2016, which is a continuation of U.S. Pat. No. 9,740,827, filed 18 Jul. 2016, which is a continuation of U.S. Pat. No. 9,600,632, filed 2 Jun. 2015, which is a continuation application of U.S. Pat. No. 9,076,317, filed 27 Aug. 2014, which is a continuation of U.S. Pat. No. 8,878,669 filed 30 Jan. 2014, which claims the benefit of U.S. Provisional Application Ser. No. 61/812,704 filed 16 Apr. 2013 and U.S. Provisional Application Ser. No. 61/759,390 filed 31 Jan. 2013, which are each incorporated in their entirety herein by this reference.

TECHNICAL FIELD

This invention relates generally to the intoxication monitoring device field, and more specifically to a new and useful method and system for monitoring intoxication.

BACKGROUND

It is often desirable to analyze a biological sample from a person to detect substances carried in the biological sample. As such, breathalyzer devices are used to test the content of alcohol (i.e., ethanol) carried in an individual's breath, in order to determine a measure of alcohol consumed by the individual. The measure is typically presented as a blood alcohol content (BAC), which can provide an indication of a user's mental and/or physical adeptness. As such, BAC measures are also used to provide a basis for limits of alcohol consumption in relation to the performance of tasks, including driving a vehicle, operating machinery, and performing various tasks in a working environment. While current blood alcohol measuring devices are able to determine an individual's BAC, and are typically used in law enforcement settings, existing systems and methods configured to provide monitoring of alcohol consumption are severely limited.

There is thus a need in the intoxication monitoring device field to create a new and useful method and system for monitoring intoxication. This invention provides such a new and useful method and system.

BRIEF DESCRIPTION OF THE FIGURES

FIGS. 7A-7C depict schematics of embodiments of a system for monitoring intoxication.

DESCRIPTION OF THE PREFERRED EMBODIMENTS

The following description of the preferred embodiments of the invention is not intended to limit the invention to these preferred embodiments, but rather to enable any person skilled in the art to make and use this invention.

1. Method

Figure 1:
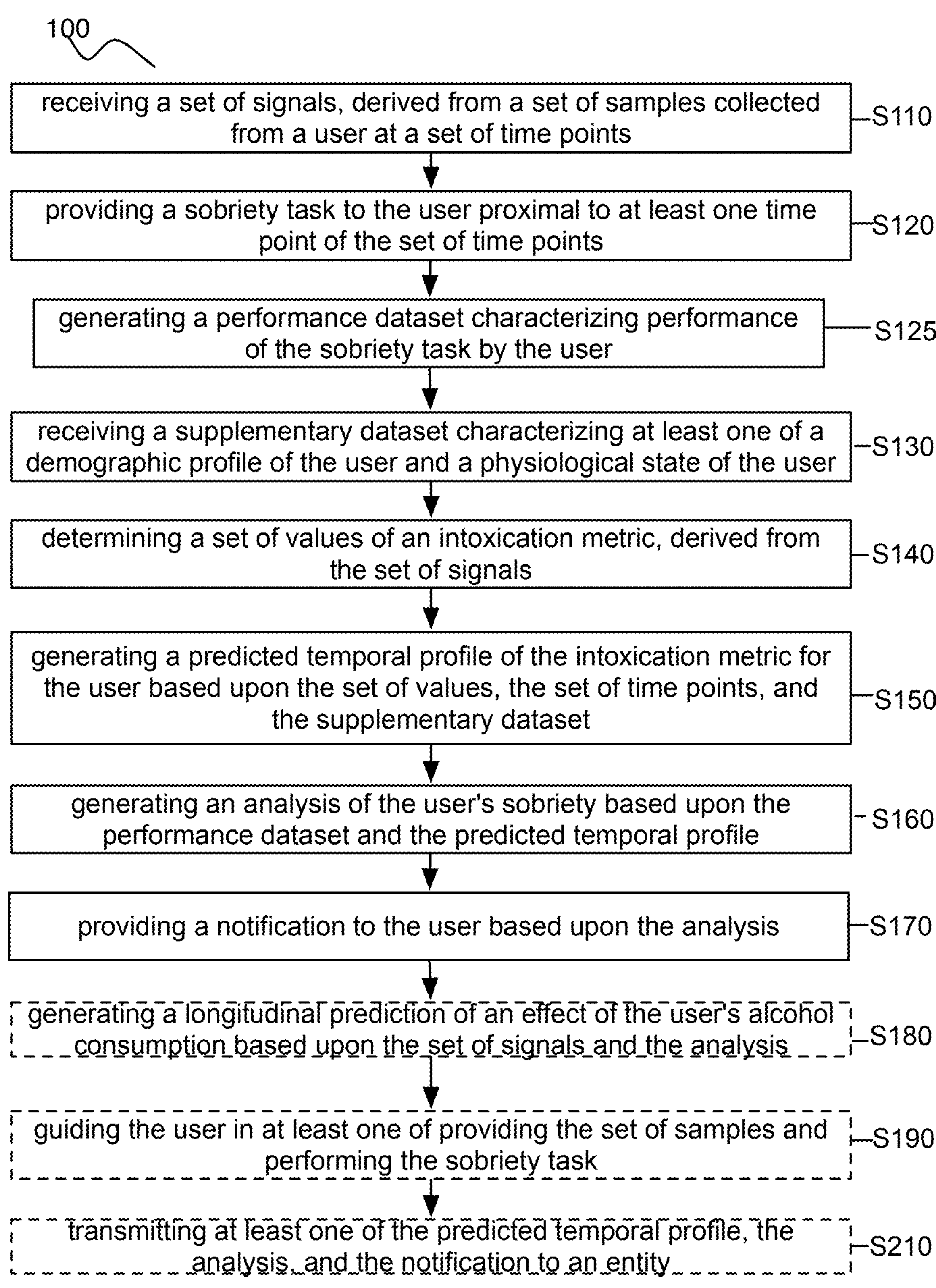
FIG. 1 depicts a schematic of an embodiment of a method for monitoring intoxication.

As shown in FIG. 1, an embodiment of a method 100 for monitoring intoxication of a user includes: receiving a set of signals, derived from a set of samples collected from the user at a set of time points Silo; providing a sobriety task to the user proximal to at least one time point of the set of time points S120; generating a performance dataset characterizing performance of the sobriety task by the user S125; receiving a supplementary dataset characterizing at least one of a demographic profile of the user and a physiological state of the user S130; determining a set of values of an intoxication metric, derived from the set of signals S140; generating a predicted temporal profile of the intoxication metric for the user based upon the set of values, the set of time points, and the supplementary dataset S150; generating an analysis of the user's sobriety based upon the performance dataset and the predicted temporal profile S160; and providing a notification to the user based upon the analysis S170. The method 100 can further comprise generating a longitudinal prediction of an effect of the user's alcohol consumption, based upon the set of signals and the analysis S180; guiding the user in at least one of providing the set of samples and performing the sobriety task S190; and transmitting at least one of the predicted temporal profile, the analysis, and the notification to an entity S210.

The method 100 functions to provide a tool that allows a user to monitor his/her alcohol consumption and behavioral effects of intoxication in a compelling and intuitive manner. The method 100 can also function to guide a user's behavior at various stages of intoxication, by providing notifications related to the user's intoxication state. In this regard, the method 100 can provide short-term and/or long-term predictions of a state of the user, in quantitative and qualitative manners, such that the user learns about the physiological and/or behavioral effects of his/her alcohol consumption. The method 100 can also incorporate a social component, wherein information related to a user's intoxication-induced behavior and/or physiological state can be communicated to another entity (e.g., a supervisor, a caretaker, a family member, an acquaintance).

Preferably, at least a subset of the method 100 is implemented using a portion of the system 200 described in Section 2 below, comprising a sample receiving module 210 configured to receive a set of samples from the user, a data link 248 configured to communicate signals derived from the set of samples, and a processor 250 configured to receive and process data in order to generate a notification that can be provided to the user at a user interface 205; however, the method 100 can be implemented using any other suitable system configured to collect and/or transmit samples from the user, analyze the samples, and provide information regarding the user's intoxication state. In one specific example, the method 100 is implemented at least in part using a breathalyzer unit including a wireless data link, a processor 250, and a mobile device 202 executing an application with a user interface 205 configured to receive inputs and provide information to the user. As such, the method 100 is preferably implemented for a user who is substantially removed from law enforcement personnel; however, the method 100 can alternatively be implemented for a user who is in proximity to law enforcement personnel.

Block Silo recites: receiving a set of signals, derived from a set of samples collected from the user at a set of time points, and functions to enable generation of data that can be used to determine a predicted temporal profile of an intoxication metric. The set of signals is preferably received at processor, such as the processor described in Section 2 below; however, the set of signals can alternatively be received at any other suitable processing element configured to transform the set of signals into a set of values of an intoxication metric. Block Silo is preferably enabled using a sample receiving module that is configured to collect the set of samples from the user. As such, the set of samples can be collected automatically and/or manually, can be collected continuously and/or intermittently, and can be collected at regular and/or irregular intervals. Furthermore, the set of samples can include any one or more of: breath samples (e.g., samples collected at a breathalyzer unit), urine samples, blood samples, interstitial fluid samples, and any other suitable sample that can be used to assess the user's intoxication.

Preferably, the set of samples is received from the user in Block S110 in a non-invasive manner; however, the set of samples can be received in a minimally invasive or invasive manner. Furthermore, in some variations, the set of signals can be received without directly collecting samples from the user; for example, the set of signals can be generated in an indirect manner, as derived from an interaction between a stimulus and the user's body (e.g., spectrometer-based analysis of light transmitted from a user's blood vessels). In still other variations, Block S110 can entirely omit using a set of samples from the user, and instead rely upon characteristics of the user and the user's alcohol consumption (e.g., gender, mass, number of drinks consumed, time over which the drinks have been consumed, etc.) to facilitate generation of values of an intoxication metric. In one such example, data used as inputs in a Widmark formula or a derivative thereof can be received in Block S110.

In a specific example of Block S110, the set of signals can be received wirelessly using a Bluetooth transmission module incorporated into a breathalyzer unit configured to collect one or more breath samples from a user at one or more stages of intoxication. In the specific example, a sample of the set of samples can be collected at the breathalyzer unit prior to cessation of alcohol consumption by the user, and/or a sample of the set of samples can be collected at the breathalyzer unit post-cessation of alcohol consumption by the user.

Block S120 recites: providing a sobriety task to the user proximal to at least one time point of the set of time points. Block S120 functions to enable an assessment of the user's abilities (e.g., motor ability, sensory ability, cognitive ability, etc.) associated with at least one state of intoxication, as determined from the set of samples collected from the user. The sobriety task is preferably provided to the user at a user interface in an electronic format, and in some variations, can be provided to the user at a user interface of an application executing at an electronic device (e.g., mobile device) of the user. As such, the sobriety task is preferably implemented in a manner that incorporates functions enabled by sensors and components of the electronic device, including one or more of motion detection (e.g., by an accelerometer), location detection (e.g., by a GPS), audio detection (e.g., by a microphone), audio stimulation (e.g., by a speaker), visual stimulation (e.g., at a display), reaction time detection (e.g., by a user input module and a clock element), orientation detection (e.g., by a gyroscope), optical detection (e.g., at an optical sensor, at an image sensor), and any other suitable function. However, the motor still task can alternatively be provided to the user in a non-electronic format (e.g., by a supervisor, by law enforcement personnel, by a caretaker, by a family member of the user, by an acquaintance of the user).

The sobriety task is preferably presented to the user proximal in time to each time point of the set of time points wherein the user provides a sample, such that performance of the sobriety task by the user can be directly associated with an intoxication metric derived from the sample. Furthermore the sobriety task can be provided to the user with at least one round of repetition, such that deviations between repeat performances and average performance metrics can be assessed. In examples, the sobriety task can be presented to the user in any one or more of the following configurations: prior to (e.g., immediately prior to) provision of a breath sample by the user at a breathalyzer, after (e.g., immediately after) provision of a breath sample by the user at a breathalyzer, and concurrently with provision of a breath sample by the user at a breathalyzer. However, in other variations, the sobriety task can additionally or alternatively be provided to the user substantially removed in time from a time point at which a sample is provided by the user, such that performance of the sobriety task by the user is not directly associated with an intoxication metric derived from a collected sample. In these variations, the user's performance of the sobriety task can, for example, be associated with a predicted value of an intoxication metric (e.g., from the predicted temporal profile generated in Block S150), or can, for example, be used to predict the value of an intoxication metric of the user without collection of a sample from the user.

The sobriety task can include a single task configured to enable an assessment of the user's abilities (e.g., motor ability, sensory ability, cognitive ability, etc.) associated with at least one state of intoxication, and in one variation, can include a test configured to gage a user's reaction to certain stimuli. In one example, the user can be presented with one or more stimuli (e.g., an audio stimulus, a visual stimulus, etc.), and the sobriety task can be used to assess the user's reaction (e.g., the user has a reaction response, the user does not have a reaction response) to the stimulus/stimuli. In another example, the user can be presented with one or more stimuli (e.g., an audio stimulus, a visual stimulus, etc.), and the sobriety task can be used to assess the user's reaction time to respond to the stimulus/stimuli. In another example, the user can be presented with a cognitive task (e.g., problem-solving task), and the user's ability to accomplish the cognitive task can assessed in Block S160. In yet another example, the user can be presented with a cognitive task (e.g., problem-solving task), and the duration required by the user to accomplish the cognitive task can be assessed in Block S160. However, the sobriety task can additionally or alternatively include any other suitable task.

Figure 2:
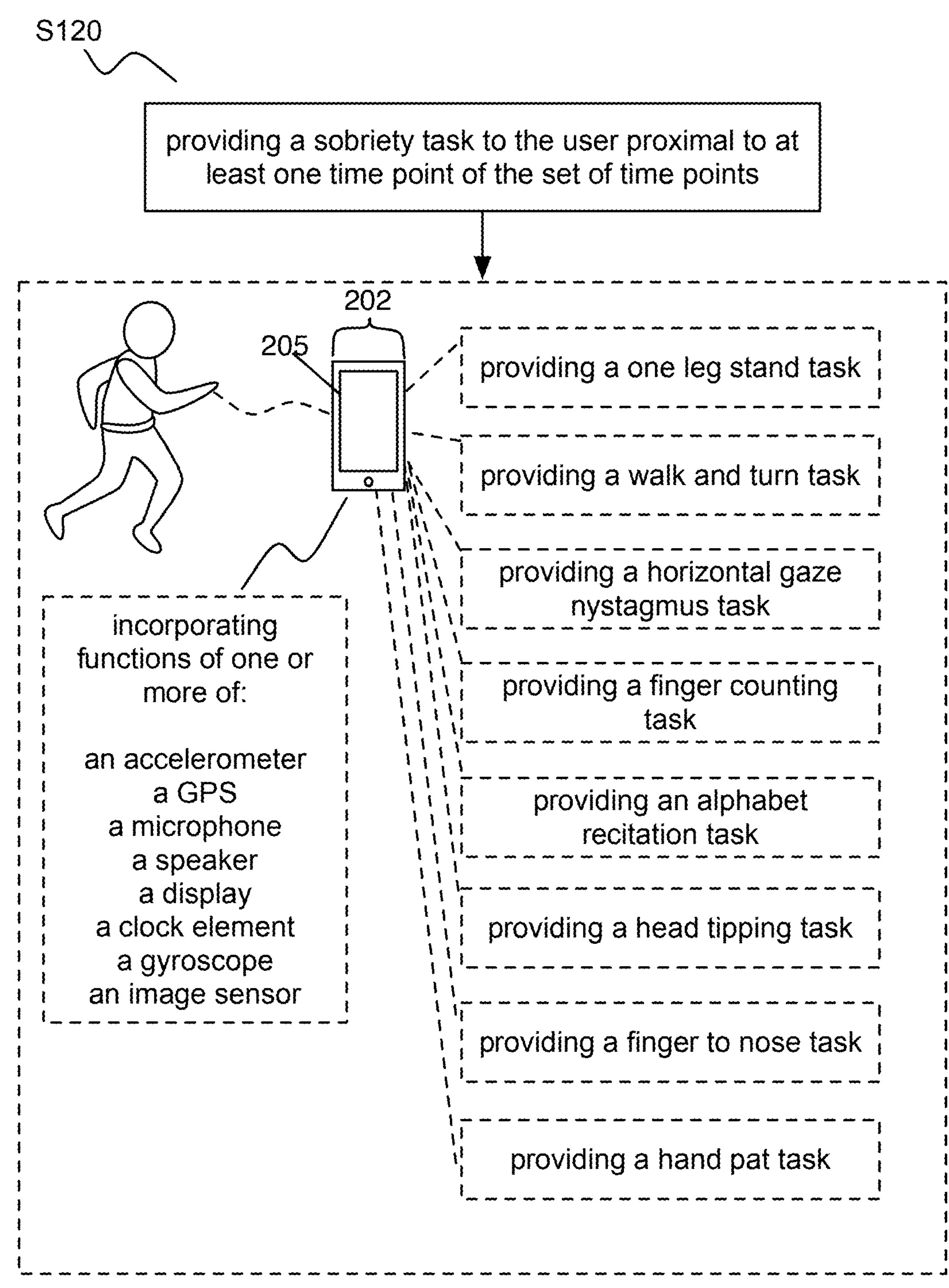
FIG. 2 depicts a schematic of a portion of an embodiment of a method for monitoring intoxication.

In other variations, the sobriety task can include a set of tasks, which can be provided in a consistent sequence whenever the user is provided with the sobriety task(s), in a random sequence, in an adaptive sequence (e.g., based upon the user's performance of a task of the set of tasks), and/or in any other suitable sequence. Furthermore, in embodiments wherein the sobriety task includes a set of tasks, the complete set of tasks can be provided to the user upon provision of the sobriety task to the user, or an incomplete set of tasks can be provided to the user, based upon a selection from the complete set of tasks by the user or by another entity. In some variations, as shown in FIG. 2, the set of tasks can be substantially identical to or analogous to tasks provided during a field sobriety test conducted by law enforcement personnel. In specific examples, the set of tasks can be configured to mimic field sobriety tests standardized by the National Highway Traffic and Safety Administration (NHTSA) of the United States of America, which include a one-leg stand (OLS) task, which requires a user to stand on one leg for 30 seconds to assess balance and coordination, a walk and turn (WAT) task, which assess a user's ability to balance and have his/her attention divided, and a horizontal gaze nystagmus (HGN) task, which assess involuntary jerking of the user's eye(s), indicative of intoxication. In variations of these examples, the set of tasks can additionally or alternatively include tasks configured to mimic tasks of any non-standardized sobriety tests, including one or more of: a finger counting (FC) task configured to assess cognition and vision, an alphabet recitation (AR) task, a counting task, a task wherein the user stands and slowly tips his/her head back, which enables an assessment of balance, a finger-to-nose (FTN) task configured to assess motor acuity, a hand-pat test, wherein the user alternatingly pats one hand with the palm and the back side of the other hand, and any other suitable task.

In specific examples, wherein a set of tasks configured to mimic a field sobriety test is provided using an application executing at a mobile device of the user, the set of tasks are implemented in a manner that incorporates functions enabled by sensors and components of the electronic device. In one example, the OLS task can incorporate image sensor functions, accelerometer functions, gyroscope functions, and or clock functions to detect that the user is standing upon one leg (e.g., as enabled by the image sensor), and that the user has maintained balance for at least 30 sections (e.g., as enabled by the accelerometer, the gyroscope, and/or the clock). In another example, the WAT task can incorporate image sensor functions, accelerometer functions, and gyroscope functions to detect that the user is walking, is walking in a straight line, and is performing walking tasks according to instructions provided at a display and/or by the speaker of the mobile device. In another example, the HGN task can incorporate a moving visual stimulus at the display of the mobile device and optical sensor functions that track an eye of the user as the user visually follows the moving visual stimulus. In another example, the FC task can present a number of objects at the display of the mobile device, and the user can be instructed to identify and input the number of objects presented. In another example, the alphabet recitation task/counting task can instruct the user to recite a portion of the alphabet or count in any order, and a microphone of the mobile device can enable an assessment of the user's accuracy in reciting and/or counting. In yet another example, the FTN task can incorporate optical sensor functions, accelerometer functions, and gyroscope functions to detect the motion of the user as the user brings the mobile device in an outstretched hand to his/her nose, and has successfully performed the task (e.g., by the optical sensor).

Block S125 recites: generating a performance dataset characterizing performance of the sobriety task by the user, and functions to analyze the user's performance of the sobriety task. The performance dataset preferably characterizes the user's abilities (e.g., motor ability, sensory ability, cognitive ability, etc.) associated with at least one sample of the set of samples, in a quantitative manner. However, the performance dataset can additionally or alternatively characterize the user's abilities in a qualitative manner. As such, the performance dataset can include quantified values of aspects of the user's performance of the sobriety task, including one or more of: total response time (e.g., response time to complete a task), average response time across repeat performances of the sobriety task, deviation in response time between repeat performances of the sobriety task, total reaction time (e.g., reaction time to a stimulus), average reaction time across repeat performances of the sobriety task, deviation in reaction time between repeat performances of the sobriety task, and any other suitable quantified variable. Additionally or alternatively, the performance dataset can include qualitative aspects of the user's performance of the sobriety task, including one or more of: performance success (e.g., the user accomplished the task, the user did not accomplish the task), performance speed (e.g., fast, medium, slow), reaction response (e.g., user reacted, user did not react), and any other suitable qualitative characteristic. As such, the performance dataset provides data that can be used to analyze the user's sobriety in Block S160.

Block S130 recites: receiving a supplementary dataset characterizing at least one of a demographic profile of the user and a physiological state of the user, and functions to provide enriching data that can be used to increase the accuracy of the set of values of the intoxication metric determined in Block S140 and/or the predictive power of the predicted temporal profile generated in Block S150. The supplementary dataset is preferably received at processor, such as the processor described in Section 2 below; however, the supplementary dataset can alternatively be received at any other suitable processing element configured to use the supplementary dataset in generating a set of values of an intoxication metric. In Block S130, the demographic profile can include any one or more of information related to: gender (e.g., male, female, etc.), age, weight, height, ethnicity, marital status, profession, geographic location, diagnosed medical conditions (e.g., diabetes, alcohol intolerance), metabolic profile (e.g., fat/muscle content), family history, genetic information, and any other suitable type of demographic-related information. In Block S130, the physiological state of the user can be determined based upon any one or more of information related to: food consumption (e.g., amount/rate of consumption), beverage consumption (e.g., amount/rate of consumption), medication usage, activity (e.g., exercise, rest, sleep), biometric information (e.g., heart rate, respiration rate, pupilometric information, neural activity information, etc.), emotional state (e.g., stress state), and another other suitable type of physiological state-related information. The supplementary dataset can, however, include any other suitable type of data in addition to demographic data and/physiological state data.

The supplementary dataset received in Block S130 can be generated by manual input (e.g., by manual input from the user) and/or automatically based upon accessing of information databases relevant to the user. In variations wherein the supplementary dataset is generated by manual input, the user or another entity can manually input demographic information and/or information related to physiological state at a user input device, which is received as the supplementary dataset. In variations wherein the supplementary dataset is generated automatically, the supplementary dataset can be generated at an aggregation module configured to access, retrieve, and/or aggregate content (e.g., digital content) from different sources (e.g., social network accounts, search results, etc.). As an example, the supplementary dataset can be generated by an aggregation module configured to access and retrieve content from the user's Facebook, Twitter, and Instagram accounts, which can be used to provide demographic information, location information, and activity information (e.g., exercise regimen information, consumption information) related to a physiological state of the user. In another example, the supplementary dataset can be generated using a module configured to extract food and/or beverage consumption information from image and/or text data. The image/text data can be input by the user by way of an application executing at an electronic device (e.g., mobile device) of the user, wherein the electronic device comprises an image sensor; however, in variations of this example the image data can additionally or alternatively be accessed and retrieved using an aggregation module in communication with the user's digital networks (e.g., digital social networks). As such, object recognition (e.g., of food items, of beverage items) and/or text recognition (e.g., of food labels, of drink labels) can be used to enable automatic identification of items that the user consumes, thus enriching the supplementary dataset. The image/text data can also be time stamped, such that the user's consumption activity can be associated in time with at least one time point of the set of time points, to facilitate generation of the predicted temporal profile in Block S150.

In the above examples and variations, the supplementary dataset preferably includes temporally static information (e.g., demographic information) and temporally varying information (e.g., physiological state information), but can include only temporally static information, only temporally varying information, and/or any other suitable type of information. Preferably, each piece of temporally varying information has an associated time stamp that is automatically retrieved and/or generated, such that the information can subsequently be associated with temporally varying intoxication states of the user predicted in variations of Block S150. However, the temporally varying information can additionally or alternatively be retroactively time-stamped (e.g., by a user, by another entity) in order to incorporate temporal information in the supplementary dataset.

Block S140 recites: determining a set of values of an intoxication metric, derived from the set of signals, and functions to determine at least one value of an intoxication metric that can be used to create one or more anchoring points for the predicted temporal profile generated in Block S150. The intoxication metric is preferably a blood alcohol concentration (BAC), which can be determined from signals generated from one or more of: a breath sample, a urine sample, a blood sample, and any other suitable biological sample from the user, as described in relation to Block S11*o* above; however, the intoxication metric can alternatively be any other suitable metric characterizing intoxication of the user. In variations wherein the set of signals is derived from breath samples of the user, a BAC value corresponding to each breath sample can be determined based upon the magnitude of an electrical signal produced when alcohol in the user's breath reacts with a sensing element of the sensor (e.g., a current magnitude produced by a platinum-alcohol oxidation reaction for a fuel cell sensor, a change in electrical resistance produced by an alcohol-dioxide reaction for a semiconductor sensor, etc.). In other variations, a BAC value corresponding to any other suitable type of sample from the user can be determined based upon an electrical signal produced in response to irradiation of the sample (e.g., by way of an electrical pulse generated in response to absorption of infrared light by the sample, using a spectrophotometer), by way of a detected chemical change (e.g., as exhibited by a color change) in response to a chemical reaction between the sample and a chemical additive, or in any other suitable manner.

Figure 3A:
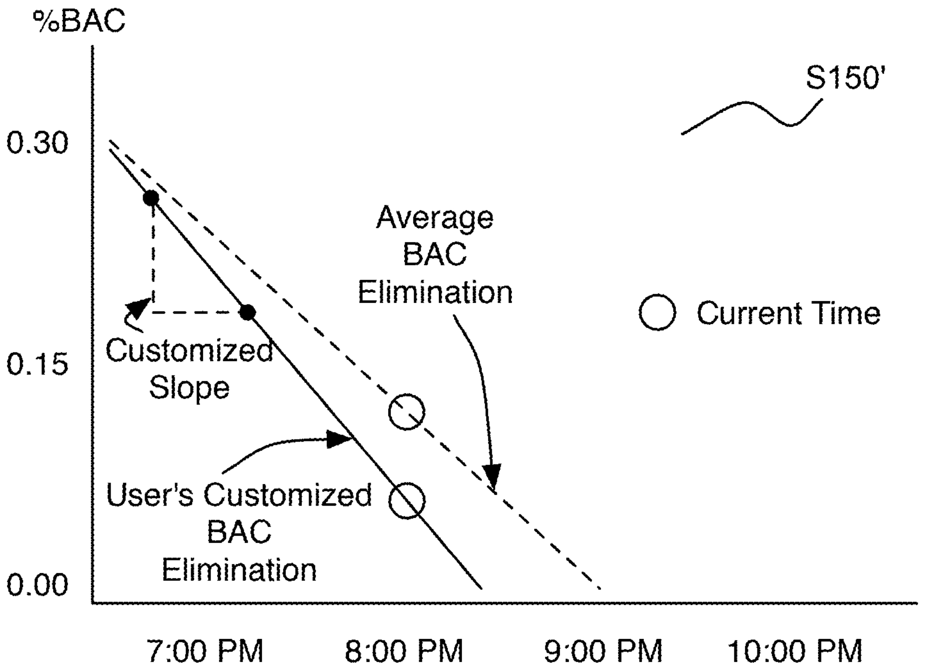
FIGS. 3A-3C depict embodiments of generating a predicted temporal profile that facilitates monitoring of the user's intoxication.

Block S150 recites: generating a predicted temporal profile of the intoxication metric for the user based upon the set of values, the set of time points, and the supplementary dataset, and functions to create a predicted temporal profile of an intoxication metric that is customized to the user and provides information regarding the user's past, present, and future states of intoxication in a quantitative and/or qualitative manner. When an individual consumes alcohol, their level of intoxication (e.g., as assessed by a BAC), will generally rise as alcohol is absorbed by their body, and then fall back to zero as alcohol is absorbed by their body. As such, the predicted temporal profile characterizes an intoxication metric vs. time for the user, which can be used to predict when the intoxication metric for a user will reach a specific value at a point in time. The predicted temporal profile can thus be generated based upon the set of values of the intoxication metric generated in Block S140 as anchoring points, as well as average profiles (e.g., rates) of alcohol absorption and elimination as determined previously from a population of individuals. Furthermore, generation of the predicted temporal profile can include forward and/or retrograde extrapolation of unknown future and/or past values of the intoxication metric, in relation to the set of values generated in Block S140. In an example, as shown in FIG. 3A, one value of an intoxication metric, determined for a time point after which the user has ceased alcohol consumption, can provide an anchoring point for a region of the predicted temporal profile over which the user's intoxication is declining, and average rates of alcohol elimination as determined from a population of individuals can be used to extrapolate the decline of the intoxication metric for the user over time, as depicted in the graphic labeled as S150' in FIG. 3A. Thus, if the user's BAC (i.e., the intoxication metric) is 0.03% at a first time point of the set of time points and an average elimination rate for a population of individuals is 0.015% per hour, the predicted temporal profile can characterize a decline in the user's BAC from 0.03% at the first time point to 0.00% two hours from the first time point. In another example, also shown in FIG. 3A, two values of an intoxication metric, determined for time points after which the user has ceased alcohol consumption, can be used to determine a slope for a region of the predicted temporal profile over which the user's intoxication is declining. Thus, if the user's BAC (i.e., the intoxication metric) is 0.05% at a first time point and 0.03% one hour after the first time point, the predicted temporal profile can characterize a decline in the user's BAC at a rate of 0.02% per hour, which is a customized rate for the user.

Figure 3B:
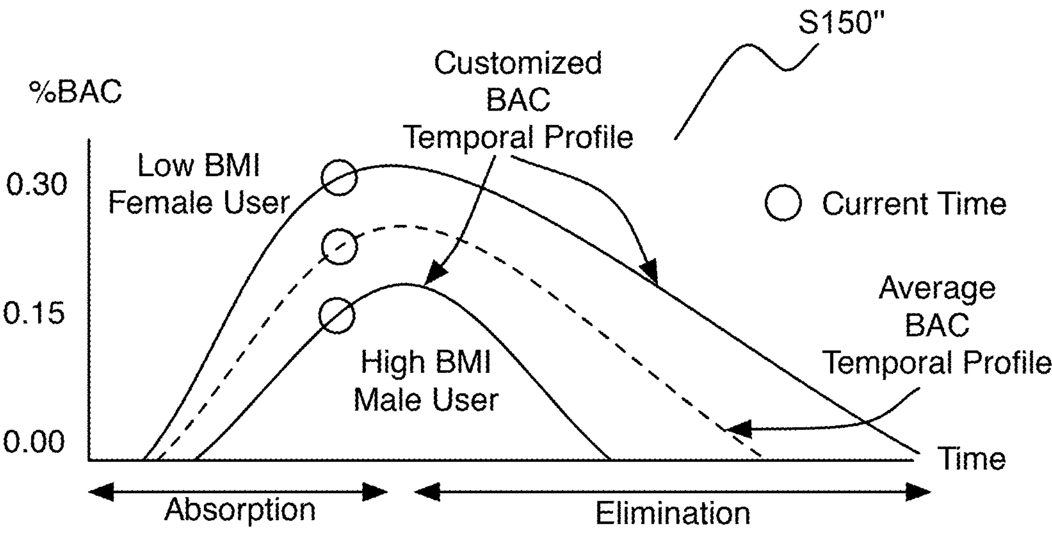

In the above variations and examples, the predicted temporal profile, including regions of rising, peaking, and declining intoxication, can further be adjusted and customized to the user, based upon the supplementary dataset. In variations, the user's alcohol absorption profile and/or elimination rate can be adjusted based upon the demographic profile of the user, as shown in FIG. 3B, as contained in the supplementary information. In one example, the predicted temporal profile can incorporate assumptions of a decreased alcohol absorption rate, an increased alcohol elimination rate and/or a BAC lower than average across all time points for a given number of alcoholic drinks consumed, given that the user is a male in his early 20's with a higher than average body mass index, a low fat-to-muscle ratio, and a family history of high tolerance to alcohol. In another example, the predicted temporal profile can incorporate assumptions of an increased alcohol absorption rate, a decreased alcohol elimination rate and/or a BAC higher than average across all time points for a given number of alcoholic drinks consumed, given that the user is a post-menopausal diabetic female with a lower than average body mass index, a high fat-to-muscle ratio, and a family history of low tolerance to alcohol. These examples are depicted in the graphic labeled as S150" in FIG. 3B. In another example, the predicted temporal profile can incorporate assumptions of an increased alcohol absorption rate, a decreased alcohol elimination rate and/or a BAC higher than average across all time points for a given number of alcoholic drinks consumed, given that the user has been diagnosed with any one or more of: deficiencies in alcohol dehydrogenase, deficiencies in aldehyde dehydrogenase, diabetes, hypertension, depression, and epilepsy. As such, the predicted temporal profile can be adjusted relative to a population average profile of intoxication characteristics, based upon specific demographic features of the user.

In variations of Block S150, the user's alcohol absorption profile and/or elimination rate can be additionally or alternatively adjusted based upon the user's physiological or metabolic state, as contained in the supplementary dataset. As such, as shown by the graphic labeled S150''' in FIG. 3C, data related to any one or more of: food consumption, beverage consumption, medication usage, activity, biometric information, emotional state, and any other suitable factor near a time point represented in the predicted temporal profile can be used to adjust an alcohol absorption profile and/or elimination rate. In one example, a region of rising intoxication in the predicted temporal profile can incorporate a decreased alcohol absorption rate and a lower peak BAC value post-consumption of a large meal, as identified within image data contributing to the supplementary dataset. In one example, a region of falling intoxication in the predicted temporal profile can incorporate an increased alcohol elimination rate post-consumption of a large meal, as identified within image data contributing to the supplementary dataset. In another example, a region of rising intoxication in the predicted temporal profile can incorporate an increased alcohol absorption rate and higher peak BAC value upon determination that the user is consuming alcohol on an empty stomach, as identified with the supplementary dataset (e.g., no images showing food consumption, no user input of information relating to a consumed meal, no check-ins at a food vendor location, GPS-based determination that the user has not visited a food vendor, etc.). In another example, a region of rising intoxication in the predicted temporal profile can incorporate an increased alcohol absorption rate and higher peak BAC value if the supplementary dataset includes biometric data indicating that the user is experiencing stress (e.g., fast heart rate, fast respiration rate, large pupil diameter, high neural activity, etc.). In another example, a region of rising intoxication in the predicted temporal profile can incorporate an increased alcohol absorption rate and higher peak BAC value if the supplementary dataset includes data indicating that the user has consumed carbonated beverages (e.g., as identified using image data).

Figures 3C, 4:
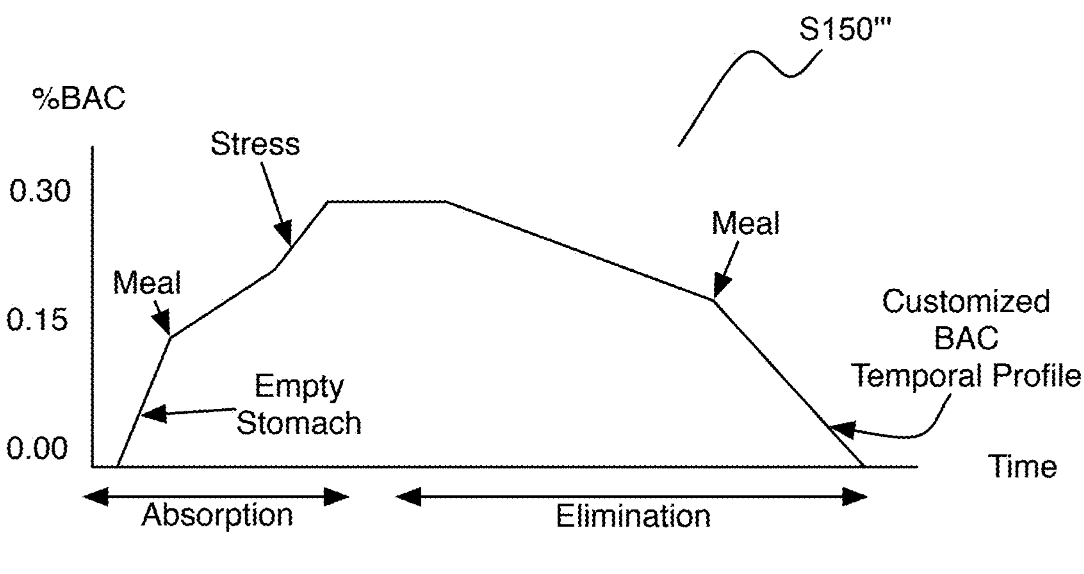
FIG. 4 depicts an example of an analysis, notification, and device/user interface configured to facilitate monitoring of the user's intoxication.

In any of the above variations and examples, customized aspects (e.g., elimination rates, absorption rates, intoxication peak characteristics, etc.) of the user's predicted temporal profile can be stored, used, and/or re-evaluated for future assessments of the user's intoxication. As such, a historical dataset (e.g., including at least one previously generated performance dataset and at least one previously generated predicted temporal profile) from the user can be used to refine predictions of alcohol absorption and/or elimination characteristics of the user, to increase the accuracy of the predicted temporal profile. In some variations, the method 100 can further include generating a prediction of a present value of the intoxication metric for the user, based upon the user's performance of the sobriety task (e.g., from the performance dataset). Thus, in an example, a user's score on the sobriety task can be used to determine an approximate current BAC value for the user, for instance, when the user is not near a sample receiving module. Furthermore, as shown in FIG. 4, the users predicted temporal profile can be rendered in some visual form (e.g., graphical form, text-based form), which can be provided to the user or other suitable entity (e.g., as part of Block S170) an example of which is labeled as S155 in FIG. 4. In examples, a predicted temporal profile of BAC vs. time, customized to the user, can be rendered as a line graph with selectable regions that associate future time points with predicted BAC values for the user. The user's customized alcohol absorption and elimination rates can also be rendered or communicated, as well as any other suitable information.

Block S160 recites: generating an analysis of the user's sobriety based upon the performance dataset and the predicted temporal profile, and functions to provide a customized analysis of the user's past, present, and/or future intoxication state(s), so that the user is able to effectively monitor his/her intoxication. The analysis preferably incorporates the predicted temporal profile, with a distribution of the intoxication metric for the user over a given time window. The analysis also preferably includes an assessment of the user's performance of the sobriety task, as determined from the performance dataset, which can be represented as one or more scores that represent the user's performance of the sobriety task at time points captured in the predicted temporal profile. For each relevant time point, the score(s) generated from the performance dataset are preferably based upon one or more of: a total response time (e.g., response time to complete a task) to complete the sobriety task, an average response time across repeat performances of the sobriety task, a deviation in response time between repeat performances of the sobriety task, a total reaction time (e.g., reaction time to a stimulus of the sobriety task), an average reaction time across repeat performances of the sobriety task, a deviation in reaction time between repeat performances of the sobriety task, and any other suitable quantified variable. Additionally or alternatively, the score(s) generated from the performance dataset can be based upon one or more of: a qualitative measure of performance success (e.g., the user accomplished the task, the user did not accomplish the task) converted to a binary score (e.g., 1=accomplishment, 0=failure), performance speed (e.g., fast, medium, slow) converted to a quantization (e.g., fast to slow performance mapped on a 1-10 scale), reaction response (e.g., user reacted, user did not react) converted to a binary score, and any other suitable factor. Thus, for at least one point on the predicted temporal profile, the analysis provides a sobriety task score that associates the user's abilities, as assessed by the sobriety task, with an intoxication state as assessed by the intoxication metric.

Figure 5A:
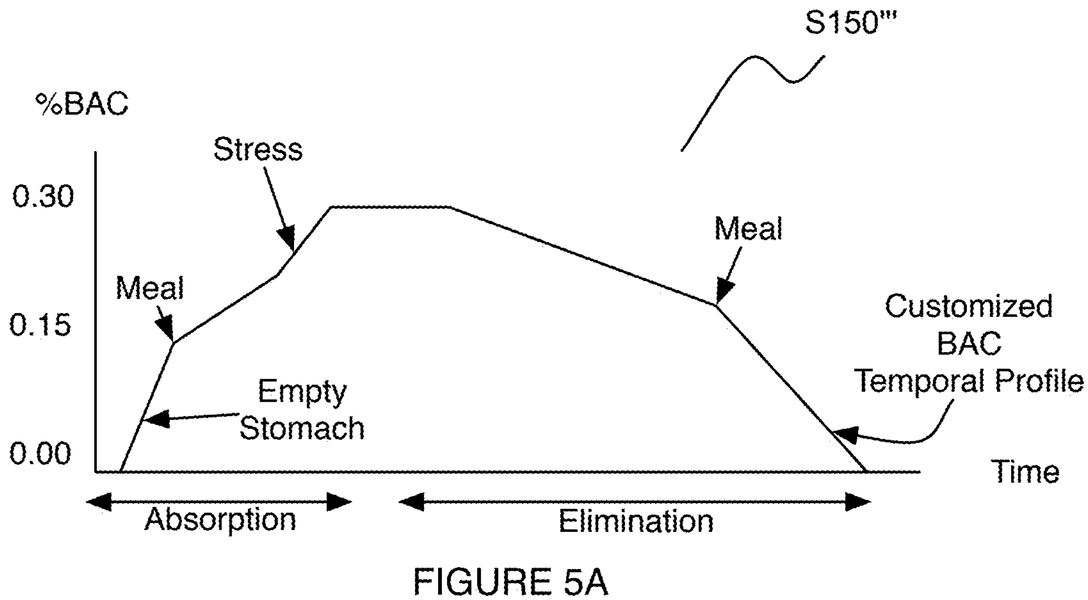
FIGS. 5A-5B depict examples of an analysis configured to facilitate monitoring of the user's intoxication.
Figure 5B:
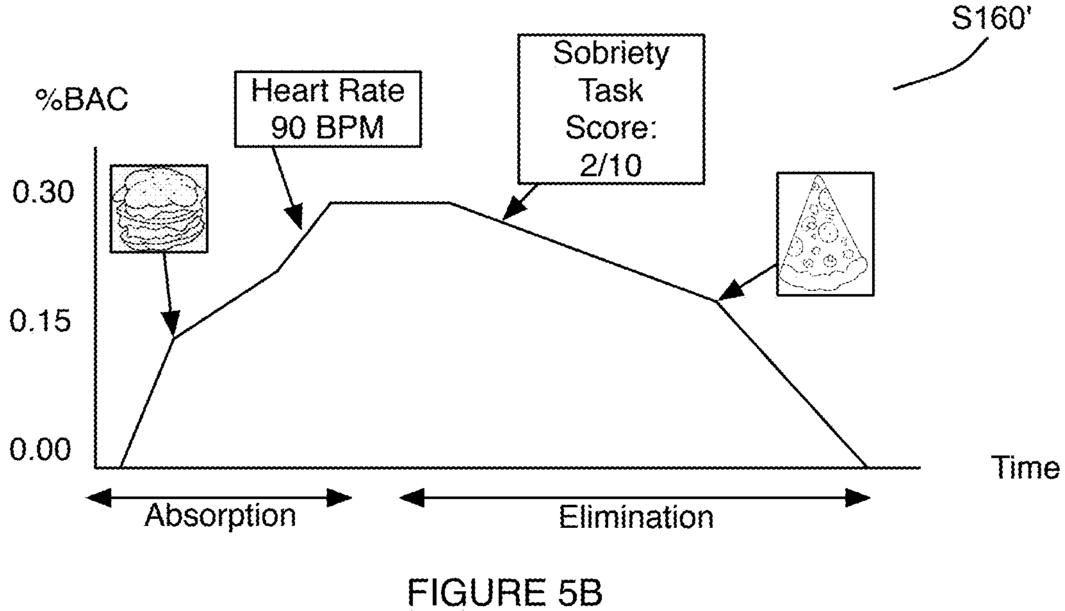

In Block S160, the analysis can also associate or annotate data points along the predicted temporal profile with user activities (e.g., meal consumption details and times, beverage consumption details and times, biometric data events, exercise events, medication events, rest events, etc.), as provided within the supplementary dataset or other suitable source. In one example, image and/or text data (e.g., images of meals, images of beverages, status updates, etc.) of the supplementary dataset can be used to annotate the predicted temporal profile, as shown in FIGS. 5A-5B, based upon time stamps of the image and/or text data, as depicted by the graphic labeled S160' in FIG. 5B. Furthermore, the analysis can be rendered in any suitable manner (e.g., tabulated format, graphical format, textual format, audio format, etc.) at a user interface or other interface, such that the comprehensive analysis is provided to the user and/or another entity. Additionally, the analysis or a derivative of the analysis can be co-presented with assumptions and factors (e.g., demographic factors, physiological state factors, etc.) used to customize the analysis to the user.

Block S170 recites: providing a notification to the user based upon the analysis, and functions to provide an alert, recommendation, and/or information that informs the user of an effect of intoxication on his/her present or future behavior. The notification can include a notification of any suitable type (e.g., visual notification, haptic notification, audio notification, etc.), and can be provided to the user in any suitable manner (e.g., using a messaging client accessible by the user, at a mobile device of the user, by a supervisor of the user, etc.). The notification can be provided automatically based upon a given alert state (e.g., an automated notification upon detection that the user is entering a dangerous intoxication state), and/or can be provided when prompted by the user or other entity. The notification preferably informs the user of his/her current intoxication state, as shown in FIG. 4, which in examples informs the user that he or she is: currently above a legal limit of intoxication (e.g., for operating a vehicle), currently below a legal limit of intoxication, or currently at an unknown intoxication state relative to a legal limit of intoxication. In further examples, the notification can inform the user that he or she is: currently below a legal limit of intoxication, but should not perform relevant activities (e.g., operating a vehicle, operating machinery) due to poor performance of the sobriety task, currently at an unknown intoxication state relative to a legal limit of intoxication, but should not perform relevant activities (e.g., operating a vehicle, operating machinery) due to poor performance of the sobriety task, or currently above a legal limit of intoxication and should not perform relevant activities, even though the user has performed the sobriety task well.

The notification can additionally or alternatively inform the user of a predicted future intoxication state, which, in examples informs the user that he or she will be: above a legal limit of intoxication (e.g., for operating a vehicle) at a future time point, below a legal limit of intoxication at a future time point, or at an unknown intoxication state relative to a legal limit of intoxication at a future time point. Furthermore, the notification regarding a predicted future intoxication state can be governed by an input from the user or other entity. As such, in variations, Block S160 can include allowing the user to input a request for information regarding a future intoxication state, and providing the notification based upon the request. In one example, a user can thus request information for when his/her BAC will return to zero (or any other suitable value), and the notification can provide an answer with or without a degree of certainty in the prediction. In another example, the user can request information regarding an effect of a consumed meal or beverage on his/her intoxication at a future time point, and the notification can provide an answer (e.g., a predicted BAC value at the future time point) with or without a degree of certainty in the prediction.

The notification can additionally or alternatively inform the user of an analyzed past intoxication state, which, in examples informs the user that he or she was: above a legal limit of intoxication (e.g., for operating a vehicle) at a past time point, below a legal limit of intoxication at a past time point, or at an unknown intoxication state relative to a legal limit of intoxication at a past time point. The notification can also be coupled with contextual information for the past time point, such as information provided in the supplementary dataset. In one example, the notification can inform the user of a BAC level at a past time point, and the location of the user when the user demonstrated the BAC level, which can help the user identify the location at which he/she lost an item in a state of inebriation. In another example, the notification can inform the user of a BAC level at a past time point, and an activity of the user (e.g., exercise activity, stress state, medication state), when the user demonstrated the BAC level, which can help the user identify correlations between the user's activities and the user's intoxication states.

The notification can additionally or alternatively indicate past, current, and/or future alcohol-induced behavior and/or impairment of the user. In variations, the notification can provide a BAC value for a past, current, or future time point, along with typical behavior and/or impairment information. In examples of these variations, the notification can include one or more of: an identified BAC in the range of 0.010-0.029, which produces normal behavior and subtle impairment effects; an identified BAC in the range of 0.030-0.059, which produces mild euphoria, relaxation, joyousness, talkativeness, decreased inhibition, and impairment of the user's concentration; an identified BAC in the range of 0.060-0.090, which produces blunted feelings, disinhibition, extroversion, impairment of reasoning, impairment of depth perception, impairment of peripheral vision, and impairment of glare recovery; an identified BAC in the range of 0.100-0.190, which produces over-expression, emotional swings, anger, sadness, boisterousness, decreased libido, impairment of reflexes, impairment of reaction time, impairment of gross motor control, impairment of speech, erectile dysfunction, and alcohol poisoning; an identified BAC in the range of 0.200-0.290, which produces stupor, loss of understanding, impaired sensations, possibility of falling unconscious, severe motor impairment, loss of consciousness, and blackout; an identified BAC in the range of 0.300-0.390, which produces severe central nervous system depression, unconsciousness, possibility of death, bladder dysfunction, breathing impairment, and disequilibrium; an identified BAC in the range of 0.400-0.500, which produces general lack of behavior, unconsciousness, possibility of death, breathing impairment, and nystagmus; and an identified BAC greater than 0.500, which produces high risk of poisoning, and possibility of death.

In some variations, Block S170 can further include enabling the user to provide an input indicative of an estimated intoxication state of the user S171, generating a comparison between the estimated intoxication state of the user and an actual intoxication state of the user S172, and providing a notification to the user, wherein the notification is configured to facilitate convergence of the estimated intoxication state and the actual intoxication state S173 in instances of future alcohol consumption. Blocks S171, S172, and S173 function to train the user in becoming more aware of his/her actual intoxication state, such that the user can more effectively estimate his/her intoxication levels during alcohol consumption. The estimated intoxication state and/or the actual intoxication state can be a past, present, or future intoxication state, such that the user can be trained to estimate past, present, and/or future states of intoxication during alcohol consumption.

In Block S171, the input is preferably provided by the user by way of an application executing at a mobile device of the user, wherein the mobile device is in communication with a processing module configured to analyze the input in relation to the actual intoxication state of the user. However, in Block S171 the input can be received by way of an input module coupled to or integrated with a system for monitoring respiration, as described in Section 2 below, and/or in any other suitable manner. In variations, Block S171 includes allowing the user to provide an estimated BAC level (e.g., past, present, or predicted future BAC level); however, any other quantitative or qualitative estimated intoxication state (e.g., cognitive ability, motor skill ability, etc.) can be provided in other variations of Block S171. The comparison generated in Block S172 preferably calculates a difference between the estimated and the actual intoxication states of the user; however, the comparison can additionally or alternatively calculate any other suitable metric (e.g., a change in difference between estimated and actual intoxication state, relative to at least one past estimate of intoxication state) configured to train the user in identifying his/her actual intoxication state at a given state in time. In Block S173, the notification can be provided to the user in any one or more of: a visual manner (e.g., at a display), a haptic manner (e.g., using a vibration motor), an auditory manner (e.g., using a speaker), and in any other suitable manner that indicates the user's level of success in predicting his/her intoxication state. In specific applications, Blocks S171-S173 can enable the user to input an estimate of his/her BAC at an input module (e.g., keyboard, touchpad, touchscreen, voice recognition module, etc.) of a mobile device included in or coupled to system for monitoring intoxication, and providing the notification at a display of the mobile device in a visual manner.

As shown in FIG. 1, the method 100 can further comprise Block S180, which recites: generating a longitudinal prediction of an effect of the user's alcohol consumption, based upon the set of signals and the analysis. Block S180 functions to enable a determination of a change in the user's alcohol tolerance level over time, which can be used to inform the user of adverse effects of alcohol consumption or abuse. The longitudinal prediction is preferably based upon accumulated analyses, such as analyses generated in multiple instances of Block S160, but can be formed based upon any other suitable data. In variations, the longitudinal prediction is based upon tracking of the user's intoxication metric values (e.g., from predicted temporal profiles) for given amounts of alcohol consumed over time, in relation to changes in any one or more of: performance of the sobriety task, behavior, impairment, weight gain, weight loss, metabolism, organ damage, organ recovery, and any other suitable expression of intoxication.

Figure 6:
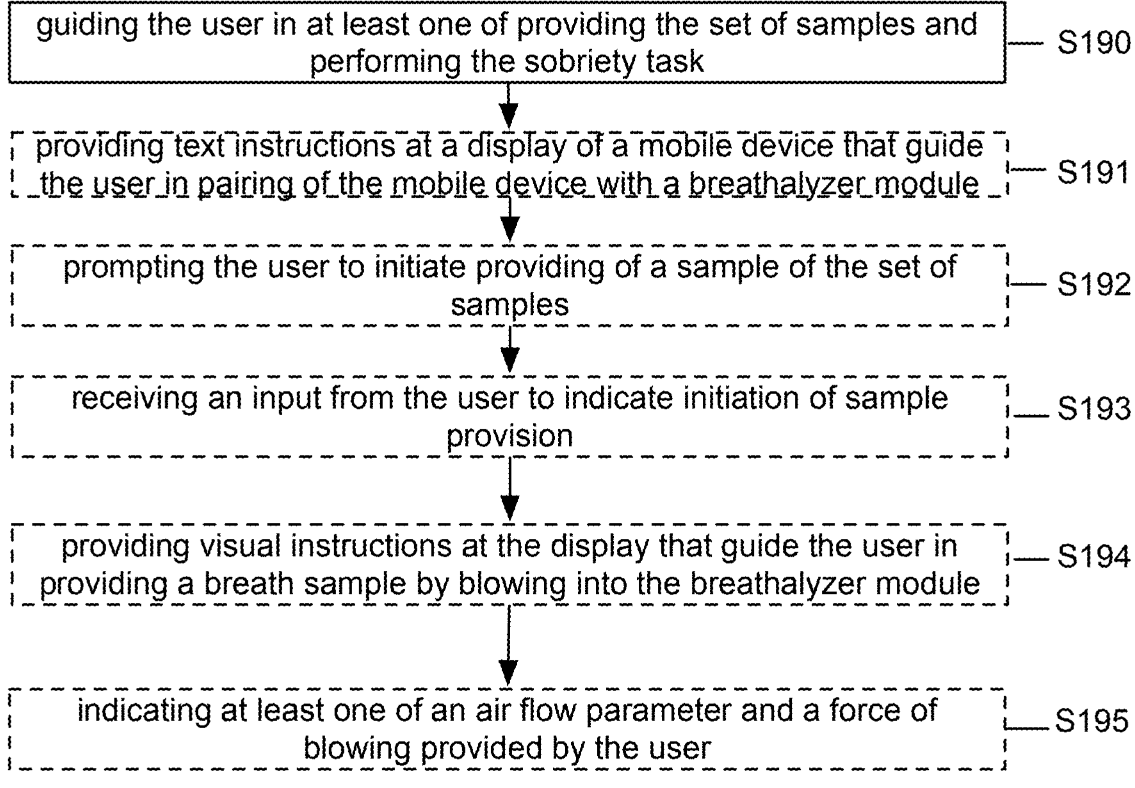
FIG. 6 depicts a schematic of a portion of an embodiment of a method for monitoring intoxication.

As shown in FIGS. 1 and 6, the method 100 can further comprise Block S190, which recites: guiding the user in at least one of providing the set of samples and performing the sobriety task. Block S190 functions to ensure that the user has provided the set of samples properly, and/or to provide the user with instructions in performing the sobriety task. In guiding the user in providing the set of samples, Block 190 is preferably implemented at a sample collection module and/or a user interface of an application executing at an electronic device (e.g., mobile device) of the user; however, guiding the user in providing the set of samples can additionally or alternatively be performed in any other suitable manner. In guiding the user in performing the sobriety task, Block 190 is preferably implemented at a user interface of an application executing at an electronic device (e.g., mobile device) of the user; however, guiding the user in performing the sobriety task can additionally or alternatively be performed in any other suitable manner. In variations of the method 100 including guiding the user in providing the set of samples, Block S190 preferably includes providing instruction to the user in one or more of a visual format, an auditory format, and a haptic format, but can additionally or alternatively include providing instruction to the user in any other suitable format. Furthermore, Block S190 can include pairing of a user interface, at which guidance of the user is provided, with a sample collection module by a wired and/or a wireless link (e.g., Bluetooth, WiFi). In examples, providing instruction can thus be implemented using one or more of a display (e.g., of a mobile device of the user and/or a display of a sample collection module), a speaker unit (e.g., of a mobile device and/or of a sample collection module), a lighting module (e.g., an LED array of a mobile device and/or of a sample collection module), and a vibration motor (e.g., of a mobile device and/or of a sample collection module).

In a specific example of guiding the user in providing the set of samples, Block S190 is implemented at a mobile device coupled with a breathalyzer module. In the specific example, Block S190 includes: providing text instructions at a display of the mobile device that guide the user in pairing of the mobile device with the breathalyzer module S191, and prompting the user to initiate provision of a sample of the set of samples S192. The specific example further includes receiving an input from the user to indicate initiation of sample provision S193 (e.g., by selecting a button, by speaking into the mobile device), which causes the mobile device to send an initiation signal to the breathalyzer module. Block S193 thus facilitates activation of the breathalyzer, which can include any one or more of warming up the breathalyzer, burning off excess alcohol, calibrating the breathalyzer, and any other suitable step. The specific example further includes providing visual instructions at the display that guide the user in providing a breath sample by blowing into the breathalyzer module S194 (e.g., by using a graphical object that indicates the amount of time that the user needs to blow into the breathalyzer). In the specific example, a microphone within the breathalyzer module senses that the user is providing the sample, and transmits a signal to the mobile device to indicate that the user is providing the breath sample. An application executing at the mobile device can then display an indicator (e.g., a countdown indicator) to guide the user in providing the breath sample over an adequate duration of time. If the user provides an inadequate breath sample, the application can provide an error notification to the user. In variations of the specific example, guiding the user can further include indicating at least one of an air flow parameter and a force of blowing (e.g., using a pressure sensor, using a flow sensor) provided by the user S195 at a display of the mobile device and/or the breathalyzer module, and indicating improper breath sample provision if the air flow parameter and/or the force of blowing does not satisfy a threshold condition S196. The specific example thus provides greater assurance that the user has properly provided a sample of the set of samples.

In variations of the method 100 including guiding the user in performing the sobriety task, Block S190 can include providing instruction to the user in one or more of a visual format, an auditory format, and a haptic format, but can additionally or alternatively include providing instruction to the user in any other suitable format. In examples analogous to those described above, providing instruction can thus be implemented using one or more of a display (e.g., of a mobile device of the user), a speaker unit (e.g., of a mobile device), a lighting module (e.g., an LED array of a mobile device), and a vibration motor (e.g., of a mobile device). The guidance in Block S190 is thus provided in a consistent format that strengthens analyses generated from the user's performance of the sobriety task.

Also shown in FIG. 1, the method 100 can further comprise Block S210, which recites: transmitting at least one of the predicted temporal profile, the analysis, and the notification to an entity. Block S210 functions to share at least one aspect related to the user's intoxication state with another entity (e.g., caretaker, friend, family member, supervisor) associated with the user, which can facilitate monitoring of the user's intoxication. The transmission preferably shares at least one of the predicted temporal profile, the analysis, and the notification in a secure manner (e.g., over a private message, with a unique URL, etc.), but can alternatively involve sharing in a non-secure manner. In variations, at least one of the predicted temporal profile, the analysis, and the notification can be provided to the entity along with any relevant activity and/or location information, as provided in the supplementary dataset. In examples, the notification can thus allow the entity to locate the user even when the user is unable or unwilling to communicate, and can prepare the entity to accommodate the intoxication state of the user (e.g., by sending a taxicab to pick the user up). In these examples and variations, the notification can also be provided in any suitable manner (e.g., messaging client, by a social network, etc.).

The method 100 can further include any other suitable blocks or steps that facilitate monitoring of a user's intoxication. Additionally, as a person skilled in the field of intoxication monitoring devices will recognize from the previous detailed description and from the figures and claims, modifications and changes can be made to the embodiments, variations, examples, and specific applications of the method 100 described above without departing from the scope of the method 100.

2. System

Figure 7B:
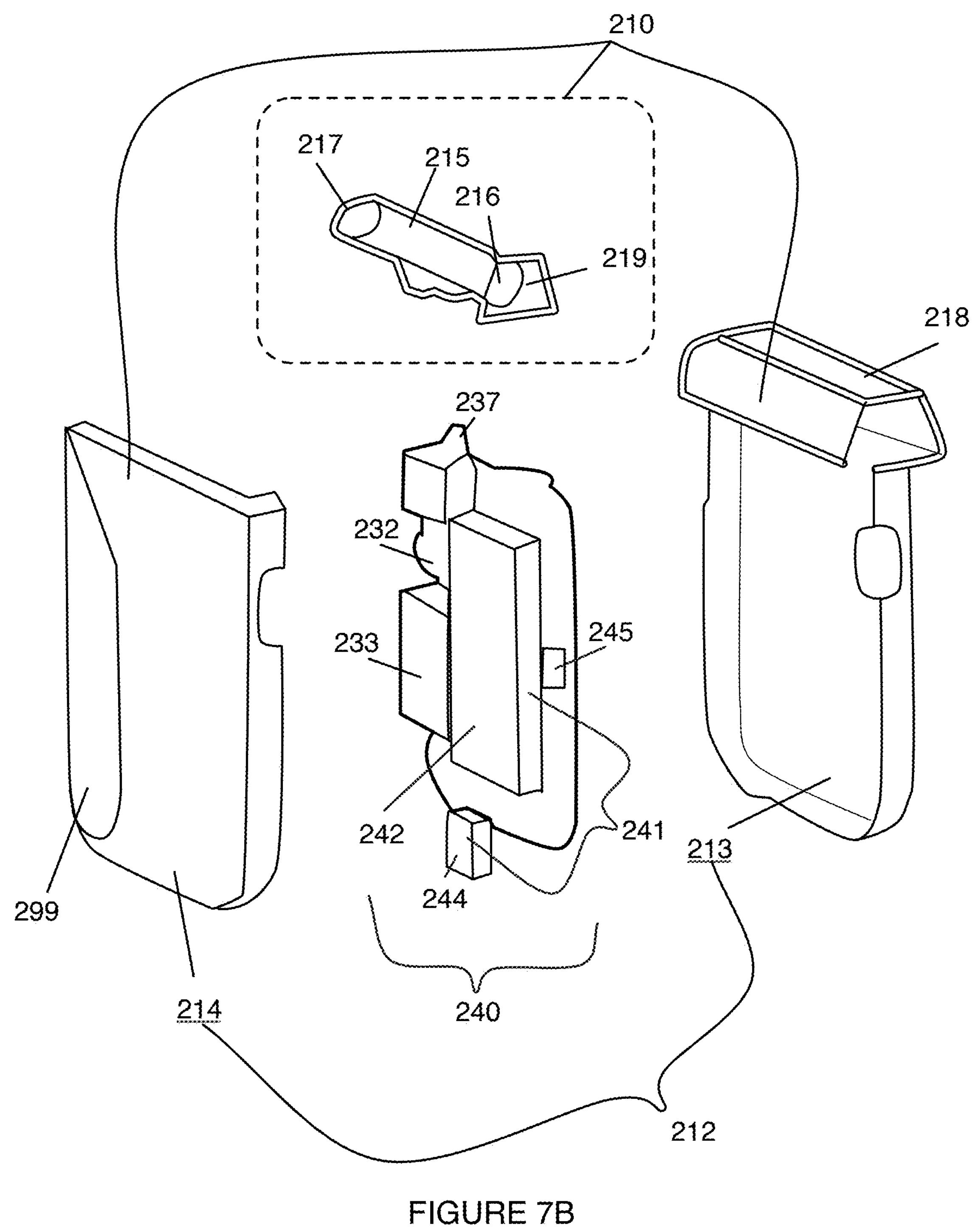
Figure 7C:
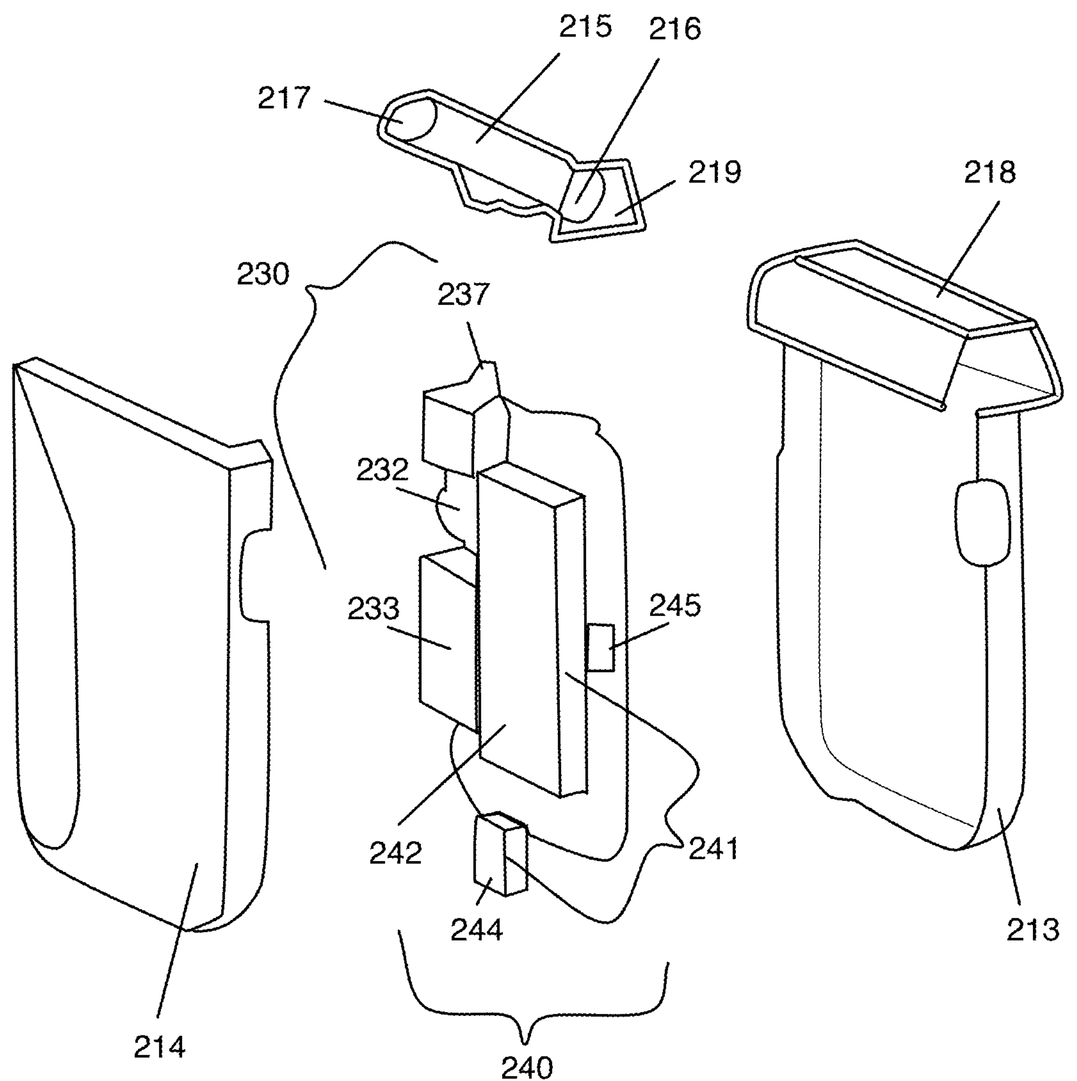

As shown in FIGS. 7A-7C, an embodiment of a system 200 for monitoring intoxication of a user includes: a sample receiving module 210 configured to accept a set of breath samples of the user at a set of time points; a sample processing module 230 configured to analyze the set of breath samples; an electronics subsystem 240 comprising a power module 241 configured to power the sample processing module 230 and a conditioning module 243 configured to process signals generated by a sensor of the sample processing module 230; a data link 248 coupled to the sample processing module and configured to communicate a set of signals derived from the set of breath samples; and a processor 250 including a first module 252 configured to receive the set of signals, a supplementary dataset, and a performance dataset characterizing the user's performance of a sobriety task proximal to at least one time point of the set of time points; a second module 254 configured to determine a set of values of an intoxication metric, derived from the set of signals; a third module 256 configured to generate a predicted temporal profile of the intoxication metric for the user based upon the set of values, the set of time points, and the supplementary dataset; a fourth module 258 configured to generate an analysis of the user's sobriety as derived from the performance dataset, and a fifth module 260 configured to generate a notification based upon the predicted temporal profile and the analysis. The system 200 can further include any other suitable element that facilitates monitoring of the user's intoxication, such as a storage module 270 configured to store and/or transmit at least one of the analysis, the notification, and the predicted temporal profile.

The system 200 functions to provide a tool that allows a user to monitor his/her alcohol consumption and behavioral effects of intoxication in a compelling and intuitive manner. The system 200 can also guide a user's behavior at various stages of intoxication, by providing notifications related to the user's intoxication state. In this regard, the system can provide short-term and/or long-term predictions of a state of the user, in quantitative and qualitative manners, such that the user learns about the physiological and/or behavioral effects of his/her alcohol consumption. The system 200 can also incorporate a social component, wherein information related to a user's intoxication-induced behavior and/or physiological state can be communicated to another entity (e.g., a supervisor, a caretaker, a family member, an acquaintance).

2.1 System—Sample Receiving Module

The sample receiving module 210 includes a body 212 defining a cavity 215 configured to accept the set of breath samples of the user at a set of time points, and functions to provide a module that facilitates reception and processing of the set of breath samples.

The body 212 is configured to enclose at least a portion of the system 200, and functions to protect elements of the system 200 over the lifetime usage of the system 200. In some embodiments, the body can further function to enhance portability of the system 200, such that the user can conveniently bring the sample receiving module wherever he/she goes. As shown in FIG. 7B, the body 212 can include a first body portion 213 and a second body portion 214 coupled together to form an interior chamber. In some variations, at least one of the first body portion 213 and the second body portion 214 can include a transparent or translucent portion 299 that allows elements within the body 212 to be visible or identifiable. However, in other variations, the first body portion 213 and the second body portion 214 can be substantially opaque to hide elements within the body 212. The body 212 is preferably composed of a polymer (e.g., polystyrene) that is processed to define features of the body (e.g., by machining, by injection molding, by casting, by printing, etc.); however, the body can alternatively be composed of any other suitable material and processed by any other suitable process. In a specific example, as shown in FIG. 7B, the first body portion 213 and the second body portion 214 couple together to form an approximately rectangular prism with rounded corners, wherein the first body portion 213 includes a transparent portion 299 located at the periphery of the first body portion 213 that allows visualization of elements internal to the body 212.

The cavity 215 is preferably included within a portion of the interior chamber of the body 212, is coupled to the sample processing module 230, and comprises a first aperture 216 and a second aperture 217, in communication with the first aperture 216, configured to facilitate sample inflow and outflow. The cavity 215 thus functions to facilitate transmission of a sample from the user to be analyzed by the sample processing module 230. The first aperture 216 and the second aperture 217 can be substantially identical in geometry, such that the cavity has an axis of symmetry (e.g., longitudinal axis of symmetry, transverse axis of symmetry), and such that each of the first aperture 216 and the second aperture 217 can function as both a sample inlet and a sample outlet; however, the first aperture 216 and the second aperture 217 can alternatively be non-identical in geometry or in any other suitable manner, as shown in FIG. 7B, such that the cavity 215 has an orientation that is identifiable by the user and is configured to only receive a sample from one of the first aperture 216 and the second aperture 217. In one variation, the cavity 215 can be defined by a tube form factor, as shown in FIG. 7B; however, the cavity 215 can alternatively be defined by any other suitable form factor that facilitates transmission of the sample from the user. The cavity 215 can be of unitary construction with the body 212, can be physically coextensive with the body 212, or can be coupled to the body 212 (e.g., to an interior portion of the body 212, to an exterior portion of the body 212) in any other suitable manner. Similar to the body 212, the cavity 215 can also include a transparent or translucent portion that can be illuminated (e.g., by a lighting module) to provide an indicator function for the user. In a specific example, as shown in FIG. 7B, the cavity 215 is partially coupled to the body 212 by a housing 218 that couples the cavity 215 to a peripheral portion of the body 212, wherein the housing 218 includes apertures that align with and provide access to the first aperture 216 and the second aperture 217.

In some variations, the sample receiving module 210 can further include a mouthpiece 219 configured to mechanically couple (e.g., with protrusions/depressions, with slots, with keys, with tabs, with threads, by press fit, etc.) to at least one of the first aperture 216 and the second aperture 217, in order to facilitate sample reception from the user. The mouthpiece 219 can be configured to permanently couple to at least one of the first aperture 216 and the second aperture 217, semi-permanently couple to at least one of the apertures 216, 217, or reversibly couple to at least one of the apertures 216, 217. Furthermore, the mouthpiece 219 can define unique identifiers (e.g., colors, textures, geometric features, etc.) that facilitate usage of the system 200 by multiple users. In one specific example, the mouthpiece 219 is configured to be reversibly coupled to the first aperture 216, such that the mouthpiece 219 is a disposable and replaceable element of the sample receiving module 210. In alternative variations of the sample receiving module 210, however, the mouthpiece 219 can be of unitary construction with one of the first aperture 216 and the second aperture 217.

2.2 System—Sample Processing Module

The sample processing module 230 is configured to couple to the cavity 215 of the sample receiving module 210, and functions to facilitate analysis of the set of breath samples and generation of a set of signals from the set of breath samples. As such, the sample processing module 230 preferably includes a sensor 232 coupled to an electronics subsystem 240, wherein the sensor interacts with a sample of the set of breath samples and the electronics subsystem 240 conditions signals produced based upon the sensor-sample interaction for transmission to a processor for further analysis. The sample processing module 230 is preferably housed within the body 212 of the sample receiving module 210, but can alternatively be configured relative to the sample receiving module 210 in any other suitable manner. The sample processing module 230 can, alternatively, include any other suitable elements that facilitate sample processing and transmission.

The sensor 232 is preferably a fuel cell sensor that enables measurement of a user's BAC by an electrochemical process. In particular, the fuel cell sensor is configured to produce an electrical current in response to oxidation of alcohol carried in a breath sample, wherein the magnitude of the produced electrical current varies in a predictable manner according to the amount (e.g., relative volume) of alcohol carried in the breath sample. As such, in some variations, the sensor 232 can be incorporated into a fuel cell subsystem including a pump 233 configured to drive a breath sample received from at least one of the first aperture 216 and the second aperture 217, through an intake 237 toward the sensor 232.

The sensor 232 can alternatively be a semiconductor sensor that produces a change in electrical resistance in response to an alcohol-dioxide reaction, wherein the magnitude of the change in resistance varies in a predictable manner according to the amount (e.g., relative volume) of alcohol carried in the breath sample. In a specific example, the semiconductor sensor can incorporate tin-oxide as a sensing element; however, variations of the semiconductor sensor can alternatively use any other suitable sensing element. In other variations of the sensor 232, the sensor can include a spectrophotometer configured to produce a signal in response to absorbed or emitted light from alcohol molecules carried in the breath sample, or any other suitable type of sensor.

The electronics subsystem 240 comprises a power module 241 configured to power the sample processing module 230 and a conditioning module 243 configured to process signals generated by the sensor 232 for transmission and further analysis. As such, the electronics subsystem 240 functions to provide power to elements of the system 200, condition and/or preprocess signals generated from received breath samples, and facilitate transmission of signals to a processor for further analysis. The electronics system 240 preferably incorporates or is configured to couple to a data link 248 for transmission of signals from the sample processing module 230 to a processor for further processing and analysis. Preferably, the electronics subsystem 240 complies with relevant technical and safety standards, such that the system 200 is configured for "home-use"; however, the electronics subsystem can be configured in any suitable manner.

The power module 241 of the electronics subsystem 240 functions to provide regulated and unregulated electrical power to the sample processing module 230 and to allow power storage for the sample processing module 230. The power module 241 preferably comprises a battery 242, such as a lithium-ion battery that is configured to be rechargeable, but can alternatively comprise any other suitable rechargeable battery (e.g., nickel-cadmium, metal halide, nickel metal hydride, or lithium-ion polymer). Alternatively, the power module 241 can comprise a non-rechargeable battery (e.g., alkaline battery) that can be replaced to further enhance modularity in the system 200. The power module 241 can be configured to have any appropriate profile such that the power module 241 provides adequate power characteristics (e.g., cycle life, charging time, discharge time, etc.) for the sample processing module 230 within physical constraints provided by the body 212 of the sample receiving module 210.

In variations where the battery 242 of the power module 241 is rechargeable, the electronics subsystem 240 can also comprise a coil of wire and associated electronics that function to allow inductive charging of the battery by an external power source and the power module 241. Inductive charging provided by the charging coil thus also facilitates patient mobility while interacting with the system 200, such that the patient can be extremely mobile while monitoring his/her intoxication. In alternative variations, however, the charging coil can be altogether omitted (e.g., in variations without a rechargeable battery), or replaced or supplemented by a connection 244 (e.g., USB connection) configured to provide wired charging of a rechargeable battery.

The conditioning module 243 functions to preprocess signals generated by the sensor 232 prior to transmission from the sample processing module 230, and can additionally function to regulate elements of the electronics subsystem 240. The conditioning module preferably comprises signal conditioning elements, including one or more of: an analog-to-digital converter (e.g., to convert analog signals sensor 232), an amplifier, and a filter for processing signals prior to transmission. In some variations, the conditioning module 243 can include a microprocessor configured to direct signal conditioning functionalities of the conditioning module 243 and a voltage regulator configured to protect elements of the electronics subsystem 240 from overvoltage and/or under-voltage states.

The electronics subsystem 240 can additionally or alternatively comprise any other suitable element that facilitates intoxication monitoring. Furthermore the electronics subsystem 240 can be coupled to a user control module 245 that interfaces with the electronics subsystem 240, such that manual control of any aspect of the sample receiving module 210 and/or the sample processing module 230 can be performed by the user or any other suitable entity. The user control module 245 can comprise a power toggle (e.g., on/off button) for activating and/or deactivating the sample receiving module 210. The user control module 245 can further include input devices that allow the user to indicate initiation of sample provision. Preferably, the user control module 245 provides a minimal number of controls (e.g., an on/off button, a sample provision initiation button), but can provide any suitable number of manual controls. The user control module 245 can be touch-activated (e.g., with a touch screen, buttons, dials, knobs, sliders), or can be activated using any other suitable manner (e.g., sound activation). Preferably, the user control module 245 is integrated with the electronics subsystem 240, but in other alternative variations, the user control module 245 can be implemented remotely from the system sample processing module 230, for example, using an application executing on a mobile device of the patient.

The data link 248 functions to transmit an output of at least one element of the electronics subsystem 240 to one or more of: a mobile device 202, a processor 250, and any other suitable computing device (e.g., desktop computer, laptop computer, tablet, smartphone, health tracking device, server, cloud). Preferably, the data link 248 is a wireless interface; however, the data link 248 may alternatively be a wired connection. In a first variation, the data link 248 can include a Bluetooth module that interfaces with a second Bluetooth module included in the mobile device or external element, wherein data or signals are transmitted by the data link 248 to/from the mobile device or external element over Bluetooth communications. The data link of the first variation can alternatively implement other types of wireless communications, such as 3G, 4G, radio, or Wi-Fi communication. In the first variation, data and/or signals are preferably encrypted before being transmitted by the data link 248. For example, cryptographic protocols such as Diffie-Hellman key exchange, Wireless Transport Layer Security (WTLS), or any other suitable type of protocol may be used. The data encryption may also comply with standards such as the Data Encryption Standard (DES), Triple Data Encryption Standard (3-DES), or Advanced Encryption Standard (AES).

In a second variation, the data link 248 is a wired connection such that the electronics subsystem 240 can communicate with the mobile device and/or any external computing element through a jack of the mobile device and/or external computing element. In one specific example of the data link 248 that includes a wired jack, the data link 248 is configured only to transmit output signals from the electronics subsystem 240. In another specific example, the data link 248 is configured to transmit data to and from at least one element of the electronics subsystem 240 and a mobile device (e.g., for pairing of the mobile device and the electronics subsystem, for synchronization between the mobile device and the electronics subsystem). In this example, the data link 248 can transmit output signals into the mobile device through the microphone input of the audio jack of the mobile device and can retrieve data from the audio output of the audio jack of the mobile device. In variations of this example, the data link 248 can additionally or alternatively communicate with the mobile device via inter-integrated circuit communication (I2C), one-wire, master-slave, or any other suitable communication protocol. However, the data link 248 can transmit data in any other way and can include any other type of wired connection (such as a USB wired connection) that supports data transfer between the electronics subsystem 240, the mobile device, and/or any other suitable computing element.

2.3 System—Processor

The processor 250 includes a first module 252 configured to receive the set of signals from the sample processing module 230, a supplementary dataset characterizing at least one of a demographic profile of the user and a physiological state of the user, and a performance dataset characterizing the user's performance of a sobriety task proximal to at least one time point of the set of time points. The processor preferably also includes a second module 254 configured to determine a set of values of an intoxication metric, derived from the set of signals; a third module 256 configured to generate a predicted temporal profile of the intoxication metric for the user based upon the set of values, the set of time points, and the supplementary dataset; a fourth module 258 configured to generate an analysis of the user's sobriety as derived from the performance dataset, and a fifth module 260 configured to generate a notification based upon the predicted temporal profile and the analysis. As such, the processor preferably functions to implement at least a portion of the method 100 described in Section 1 above, but can alternatively be configured to perform any other suitable method that facilitates monitoring of the user's intoxication. The first module 252, the second module 254, the third module 256, the fourth module 258, and the fifth module 260 can be implemented at a single processing unit, or can be implemented using multiple processing units.

2.4 System—Other Elements

The system 200 can additionally further comprise a storage module 270, which functions to retain data generated during use of the system 200. The storage module 270 can be implemented with any one or more of: the electronics subsystem 240, mobile device, personal computer, web browser, external server (e.g., cloud), local server, and any combination of the above, in a network configured to transmit, store, and receive data. Preferably, data from the storage module 270 is automatically transmitted to any appropriate external device continuously; however, data from the storage module 270 can alternatively be transmitted intermittently (e.g. every minute, hourly, daily, or weekly).

In one example, data generated by any element can be stored on a portion of the storage module 270 when the data link 248 is not coupled to an element external to the electronics subsystem 240. However, in the example, when a link is established between the data link 248 and an external element, data may then be automatically transmitted from the storage module 270. In other examples, the storage module 270 can alternatively be manually prompted to transmit stored data by a user or other entity.

As shown in FIG. 7A, the system 200 can additionally include a supplementary sensing module 280 configured to communicate with the processor 250, wherein the supplementary sensing module functions to facilitate reception and/or generation of data related to any one or more of: food consumption (e.g., amount/rate of consumption), beverage consumption (e.g., amount/rate of consumption), medication usage, activity (e.g., exercise, rest, sleep), biometric information (e.g., heart rate, respiration rate, pupilometric information, neural activity information, etc.), emotional state (e.g., stress state), user location information, and any other suitable type of supplementary information (e.g., environmental data). As such, the supplementary sensing module 280 can include any one or more of: an image sensor 281 (e.g., for generation of image data related to food, drink, or medication usage), an accelerometer 282 (e.g., for activity data), a gyroscope 283 (e.g., for activity data), a location sensor 284 (e.g., GPS), and a biometric sensor 285 (e.g., heart rate monitor, respiration sensor, blood pressure sensor, electroencephalogram activity sensor, etc.). The supplementary sensing module can also include a manual input module 286 configured to receive manual inputs from the user or another entity that provides supplementary data. In some variations, involving automated generation of a supplementary dataset as described in Section 1 above, the supplementary sensing module 280 can include an aggregation module 287 configured to access, retrieve, and/or aggregate content (e.g., digital content) from different sources (e.g., social network accounts, search results, etc), and can additionally include object recognition and/or text recognition modules 288, 289, respectively to enable automatic identification of items that the user consumes. The supplementary sensing module can additionally comprise a tagging module configured to tag supplementary data with time information to facilitate analysis and processing of data by the processor 250.

Figure 8:
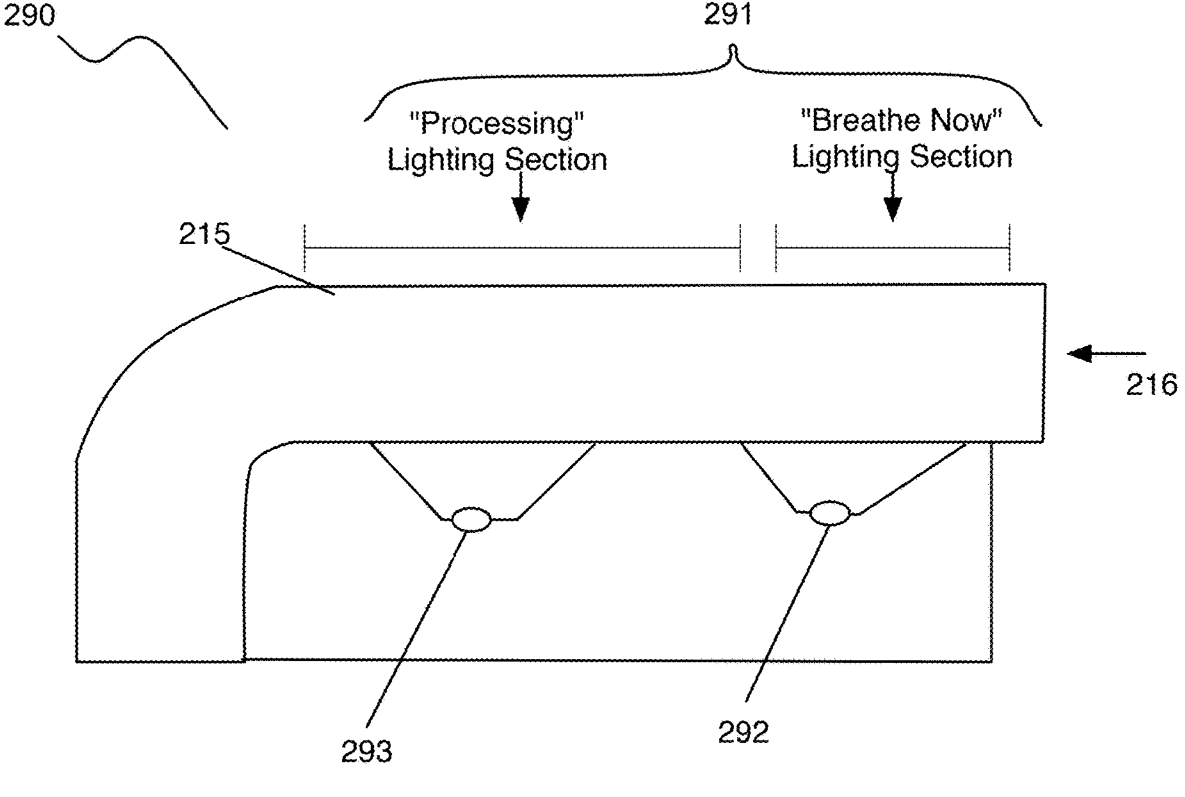
FIG. 8 depicts an example of a portion of a system for monitoring intoxication.

As shown in FIG. 8, the system 200 can additionally include an indicator module 290, which functions to guide the user in properly providing a sample of the set of samples. The indicator module 290 can be implemented using an application executing at a mobile device of the user, and in variations, can incorporate functions of one or more of: a display of the mobile device, an LED of the mobile device, a speaker of the mobile device, a vibration motor of the mobile device, and any other suitable element of the mobile device. The indicator module 290 can additionally or alternatively be implemented using a lighting module 291 configured to couple to the sample receiving module 210 and the sample processing module 230. One variation of the lighting module 291 includes a set of light emitting diodes (LEDs) configured to indicate that the user should initiate provision of a breath sample, that the sample processing module 230 is processing the breath sample, and/or that the user has improperly provided a breath sample. In a specific example, as shown in FIG. 8, the lighting module 291 includes a first LED 292 and a second LED 293 oriented proximal to the cavity 215 (e.g., a tube configured to receive the breath sample), such that the first LED 292 and the second LED 293 illuminate the cavity to provide an indicator function for the user. In the specific example, the first LED 292 functions as a visual cue that guides the user in submitting a breath sample into the cavity 215, and the second LED 293 functions as a visual cue that indicates that the sample processing module 230 is currently processing the breath sample provided by the user. As such, the first LED 292 and the second LED 293 in the specific example are both coupled to the electronics subsystem 240 of the sample processing module 230. Other variations of the indicator module 290 can include any other suitable indication elements in communication with any other suitable element of the system 200.

Variations of the method 100 and system 200 include any combination or permutation of the described components and processes. Furthermore, various processes of the preferred method can be embodied and/or implemented at least in part as a machine configured to receive a computer-readable medium storing computer-readable instructions. The instructions are preferably executed by computer-executable components preferably integrated with a system and one or more portions of the control module 155 and/or a processor. The computer-readable medium can be stored on any suitable computer readable media such as RAMs, ROMs, flash memory, EEPROMs, optical devices (CD or DVD), hard drives, floppy drives, or any suitable device. The computer-executable component is preferably a general or application specific processor, but any suitable dedicated hardware device or hardware/firmware combination device can additionally or alternatively execute the instructions.

The FIGURES illustrate the architecture, functionality and operation of possible implementations of systems, methods and computer program products according to preferred embodiments, example configurations, and variations thereof. In this regard, each block in the flowchart or block diagrams may represent a module, segment, step, or portion of code, which comprises one or more executable instructions for implementing the specified logical function(s). It should also be noted that, in some alternative implementations, the functions noted in the block can occur out of the order noted in the FIGURES. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

As a person skilled in the art will recognize from the previous detailed description and from the figures and claims, modifications and changes can be made to the preferred embodiments of the invention without departing from the scope of this invention defined in the following claims.

We claim:

1. A system for detecting intoxication of a user, the system comprising:

a breathalyzer device, the breathalyzer device comprising:

an inlet, the inlet configured to receive a breath sample from the user;

a 1$^{st}$ display device comprising a screen at a broad surface of the breathalyzer device;

a $2^{nd}$ display device separate and distinct from the $1^{st}$ display device, the $2^{nd}$ display device comprising a set of light emitters;

a haptic device configured to provide haptic stimulation to a user proximal in time to provision of the breath sample; and a processing subsystem configured to determine an intoxication parameter based on the breath sample and control at least one of: the $1^{st}$ display device, the $2^{nd}$ display device, or the haptic device based on the intoxication parameter, and to return a predicted temporal profile of the intoxication parameter, wherein a region of the predicted temporal profile includes an anchoring point determined from processing of a second breath sample.

2. The system of claim 1, wherein the inlet is at least partially defined in a mouthpiece, the mouthpiece reversibly coupleable with the breathalyzer device.

3. The system of claim 1, wherein the processing subsystem is configured to display a future prediction at the $1^{st}$ display device based on the intoxication parameter.

4. The system of claim 3, wherein the future prediction comprises a predicted future intoxication state of the user, comprising a qualitative cognitive characterization comprising problem-solving ability.

5. The system of claim 3, wherein the $2^{nd}$ display device indicates a category of a current intoxication state of the user.

6. The system of claim 5, wherein the category is indicated with a color of the lighting module.

7. The system of claim 1, wherein the $2^{nd}$ display device is arranged at a surface of the breathalyzer device perpendicular to the broad surface.

8. The system of claim 1, wherein the processing subsystem further controls the haptic device prior to determining the intoxication parameter.

9. The system of claim 8, wherein the processing subsystem controls the haptic device during receipt of the breath sample from the user.

10. The system of claim 8, wherein the processing subsystem controls the $1^{st}$ display device and the $2^{nd}$ display device based on the intoxication parameter.

11. A method for detecting intoxication of a user with a breathalyzer device, the method comprising:

with an inlet of the breathalyzer device, receiving a breath sample from the user;

processing the breath sample to determine an intoxication parameter;

displaying a $1^{st}$ set of visual information at a $1^{st}$ display device onboard the breathalyzer device;

displaying a $2^{nd}$ set of visual information at a $2^{nd}$ display device onboard the breathalyzer device;

providing vibratory stimulation at a haptic device onboard the breathalyzer device; and controlling at least one of: the $1^{st}$ display device, the $2^{nd}$ display device, or the haptic device based on the intoxication parameter, to return a predicted temporal profile of the intoxication parameter, wherein a region of the predicted temporal profile includes an anchoring point determined from processing of a second breath sample.

12. The method of claim 11, wherein the $1^{st}$ display device is separate and distinct from the $2^{nd}$ display device, wherein the $1^{st}$ and $2^{nd}$ display devices are arranged at different locations onboard the breathalyzer device.

13. The method of claim 12, wherein the $1^{st}$ display device comprises a screen and wherein the $2^{nd}$ display device comprises a set of light emitters.

14. The method of claim 11, wherein the vibratory stimulation is provided proximal in time to provision of the breath sample.

15. The method of claim 14, wherein the vibratory stimulation is provided prior to determining the intoxication parameter.

16. The method of claim 11, wherein the $1^{st}$ set of visual information comprises a future prediction determined based on the intoxication parameter.

17. The method of claim 16, wherein the future prediction comprises a predicted future intoxication state of the user based on the predicted temporal profile of the intoxication parameter, wherein the temporal profile comprises a region of rising intoxication.

18. The method of claim 16, wherein the $2^{nd}$ display device indicates a category of current intoxication of the user.

19. The method of claim 18, wherein the category is indicated with a color of the lighting module.

20. The method of claim 11, wherein the method further comprises providing the vibratory stimulation during receipt of the breath sample from the user.

* * * * *